United States Patent
Champagne et al.

(10) Patent No.: US 10,130,438 B2
(45) Date of Patent: *Nov. 20, 2018

(54) SURGICAL GLOVE WITH ERGONOMIC FEATURES

(71) Applicant: Exsomed International IP, LLC, Avarua, Rarotonga (CK)

(72) Inventors: Lloyd P. Champagne, Phoenix, AZ (US); Jozef Zoldos, Phoenix, AZ (US); Yani Deros, Phoenix, AZ (US)

(73) Assignee: EXSOMED INTERNATIONAL IP, LLC, Rarotonga (CK)

( * ) Notice: Subject to any disclaimer, the term of this patent is extended or adjusted under 35 U.S.C. 154(b) by 567 days.

This patent is subject to a terminal disclaimer.

(21) Appl. No.: 14/133,424

(22) Filed: Dec. 18, 2013

(65) Prior Publication Data

US 2014/0208480 A1    Jul. 31, 2014

Related U.S. Application Data

(63) Continuation-in-part of application No. 14/099,803, filed on Dec. 6, 2013, now Pat. No. 9,974,611.

(60) Provisional application No. 61/758,728, filed on Jan. 30, 2013, provisional application No. 61/772,463, filed on Mar. 4, 2013.

(51) Int. Cl.
*A61B 42/10* (2016.01)
*A61B 42/00* (2016.01)
*A61B 17/00* (2006.01)
*A61B 42/40* (2016.01)

(52) U.S. Cl.
CPC .............. *A61B 42/10* (2016.02); *A61B 42/00* (2016.02); *A61B 42/40* (2016.02); *A61B 2017/00424* (2013.01)

(58) Field of Classification Search
CPC ......... A61B 19/04; A61B 42/00; A61B 42/40; A61B 2017/00424; A41D 19/0055; A41D 19/0062; A41D 19/0079; A41D 19/02
USPC ................................................ 2/161.7, 161.8
See application file for complete search history.

(56) References Cited

U.S. PATENT DOCUMENTS

| | | |
|---|---|---|
| 467,974 A | 2/1892 | Healey |
| 1,279,855 A | 9/1918 | Garvey |
| D61,479 S | 9/1922 | Rice |
| 1,538,262 A | 5/1925 | Ackerman |
| 1,894,066 A | 1/1933 | Smith |
| 2,036,413 A | 4/1936 | Wendell |
| D100,816 S | 8/1936 | Fuchs |
| 2,075,550 A | 3/1937 | Smith |

(Continued)

FOREIGN PATENT DOCUMENTS

| | | |
|---|---|---|
| DE | 654995 C | 1/1938 |
| EP | 2828409 | 9/2015 |

(Continued)

OTHER PUBLICATIONS

PCT; International Search Report and Written Opinion dated Feb. 25, 2014 in Application No. PCT/US2013/073727.

(Continued)

*Primary Examiner* — Alissa L Hoey
(74) *Attorney, Agent, or Firm* — Hudak, Shunk & Farine Co. LPA

(57) ABSTRACT

Disclosed is a surgical glove that alleviates the biasing force associated with bending or abducting the hand and fingers when wearing a surgical glove.

37 Claims, 19 Drawing Sheets

(56) References Cited

U.S. PATENT DOCUMENTS

| | | |
|---|---|---|
| 2,173,734 A | 9/1939 | Sidnell |
| D133,927 S | 9/1942 | Balzano |
| 2,434,035 A | 1/1948 | De Laney |
| D164,429 S | 9/1951 | Kress |
| D179,250 S | 11/1956 | Higier |
| 2,838,759 A | 6/1958 | William |
| 3,283,338 A * | 11/1966 | Landau ............... A41D 19/0062 2/161.6 |
| 3,601,816 A * | 8/1971 | Pordes ............... A41D 19/0062 2/167 |
| 3,728,739 A | 4/1973 | Semp |
| 3,748,792 A | 7/1973 | Lamb |
| 3,789,555 A | 2/1974 | Means |
| 3,867,727 A * | 2/1975 | Povlacs ............... A41D 19/0062 2/167 |
| 3,872,514 A | 3/1975 | Liebelt |
| 3,872,515 A | 3/1975 | Miner |
| 4,000,524 A * | 1/1977 | Rinehart ................ A41D 19/02 2/161.6 |
| 4,175,593 A | 11/1979 | Sack |
| 4,218,778 A | 8/1980 | Stansbury |
| 4,441,213 A | 4/1984 | Trumble et al. |
| 4,494,249 A | 1/1985 | Hansson |
| 4,590,626 A | 5/1986 | Chen |
| 4,594,736 A | 6/1986 | Connelly |
| 4,663,783 A | 5/1987 | Obayashi |
| 4,845,780 A | 7/1989 | Reimers |
| 4,924,530 A | 5/1990 | Tagaya |
| 5,317,759 A | 6/1994 | Pierce |
| 5,323,490 A | 6/1994 | Yarbrough |
| 5,345,612 A | 9/1994 | Stein |
| D359,381 S | 6/1995 | Henriquez |
| 5,442,816 A | 8/1995 | Seketa |
| 5,500,957 A | 3/1996 | Stein |
| 5,527,244 A | 6/1996 | Waller et al. |
| D372,578 S | 8/1996 | Chapman |
| 5,636,382 A | 6/1997 | Chopko et al. |
| 5,644,797 A | 7/1997 | Daneshvar |
| D391,683 S | 3/1998 | Heringer |
| 5,728,255 A | 3/1998 | Jurrius |
| 5,781,931 A | 7/1998 | Lee |
| 5,817,433 A | 10/1998 | Darras |
| 5,907,870 A * | 6/1999 | Monroe ................ A61B 42/00 2/161.7 |
| 5,946,720 A | 9/1999 | Sauriol |
| 5,965,276 A | 10/1999 | Shlenker et al. |
| 6,081,928 A | 7/2000 | Boume |
| 6,272,687 B1 | 8/2001 | Cunningham |
| 6,575,822 B2 | 6/2003 | Lowe |
| 6,578,205 B1 | 6/2003 | King |
| D479,972 S | 9/2003 | Cueto |
| 6,732,378 B2 | 5/2004 | Novak |
| 6,760,923 B1 * | 7/2004 | Tate ....................... A61B 42/00 2/159 |
| 6,779,199 B1 | 8/2004 | O'Dea |
| D512,549 S | 12/2005 | Benjamin |
| D552,827 S | 10/2007 | Muse |
| RE40,142 E | 3/2008 | Fous |
| D567,476 S | 4/2008 | Harland |
| D605,377 S | 12/2009 | House |
| 7,694,352 B2 | 4/2010 | Kogawa et al. |
| 7,802,316 B2 | 9/2010 | Hofmann |
| D628,767 S | 12/2010 | Bengyak |
| 8,336,119 B2 | 12/2012 | Phelps |
| D677,030 S | 2/2013 | Wessels |
| 8,400,256 B2 | 3/2013 | Matthews |
| D680,695 S | 4/2013 | Lin et al. |
| 8,453,266 B2 | 6/2013 | Bevier et al. |
| 8,505,115 B2 | 8/2013 | Matsuoka |
| 8,512,615 B1 | 8/2013 | Amdur et al. |
| 8,572,765 B2 | 11/2013 | Tao |
| D707,526 S | 6/2014 | Daniel |
| D733,972 S | 7/2015 | Lawton |
| D735,968 S | 8/2015 | Furlong |
| D739,993 S | 10/2015 | Mathota |
| 9,179,718 B2 * | 11/2015 | Anstey ................ A41D 19/015 |
| D747,070 S | 1/2016 | Kelly |
| D754,929 S | 4/2016 | Champagne |
| 9,370,209 B2 | 6/2016 | Hull |
| 9,622,523 B2 | 4/2017 | Champagne |
| 2002/0166156 A1 | 11/2002 | Clark et al. |
| 2004/0255362 A1 | 12/2004 | Soerens et al. |
| 2005/0015846 A1 | 1/2005 | Vistins et al. |
| 2006/0005295 A1 | 1/2006 | Mattesky |
| 2006/0191056 A1 | 8/2006 | Bottcher |
| 2006/0218697 A1 | 10/2006 | Modha et al. |
| 2007/0074331 A1 | 4/2007 | Bitzer |
| 2008/0000010 A1 | 1/2008 | Erickson et al. |
| 2008/0134411 A1 | 6/2008 | Shapiro |
| 2008/0155726 A1 | 7/2008 | Anclien |
| 2008/0244808 A1 * | 10/2008 | Chaen ..................... A41D 19/02 2/161.2 |
| 2010/0050311 A1 | 3/2010 | Tsai |
| 2011/0258751 A1 * | 10/2011 | Matsuoka ............... A41D 19/02 2/159 |
| 2011/0277215 A1 | 11/2011 | Lee et al. |
| 2011/0296582 A1 | 12/2011 | Bevier et al. |
| 2012/0042437 A1 | 2/2012 | Matthews |
| 2012/0047616 A1 | 3/2012 | Wood |
| 2013/0061369 A1 | 3/2013 | Lim |
| 2013/0263355 A1 * | 10/2013 | Mavraganes ...... A41D 19/0027 2/161.7 |
| 2013/0291282 A1 | 11/2013 | Anstey |
| 2014/0020152 A1 | 1/2014 | Yang |
| 2014/0150162 A1 * | 6/2014 | Guan .................... A41D 19/04 2/161.7 |
| 2014/0166521 A1 | 6/2014 | Champagne et al. |
| 2014/0208481 A1 | 7/2014 | Champagne et al. |
| 2014/0259283 A1 * | 9/2014 | Govindasamy ........ A61B 19/04 2/161.7 |
| 2015/0189932 A1 | 7/2015 | Champagne et al. |
| 2016/0081408 A1 | 3/2016 | Hull |
| 2016/0174634 A1 * | 6/2016 | Schatzberg ............. B29C 41/14 2/163 |

FOREIGN PATENT DOCUMENTS

| | | | |
|---|---|---|---|
| EP | 2950739 | 11/2015 | |
| FR | 476889 A | 9/1915 | |
| FR | 1141139 A | 8/1957 | |
| GB | 2148094 A * | 5/1985 | ......... A41D 19/0062 |
| WO | 199639055 A1 | 12/1996 | |
| WO | 2013126727 A1 | 8/2013 | |

OTHER PUBLICATIONS

PCT; International Search Report and Written Opinion dated Apr. 17, 2014 in Application No. PCT/US2014/013940.
USPTO; Office Action dated Jun. 17, 2015 in U.S. Appl. No. 14/542,217.
USPTO; Notice of Allowance dated Dec. 19, 2016 in U.S. Appl. No. 14/542,217.
USPTO; Office Action dated Feb. 7, 2017 in U.S. Appl. No. 14/099,803.
USPTO; Notice of Allowance dated Dec. 10, 2015 is U.S. Appl. No. 29/475,635.
USPTO; Office Action dated May 18, 2016 in U.S. Appl. No. 14/542,217.
USPTO; Restriction Requirement dated May 20, 2016 in U.S. Appl. No. 14/099,803.
USPTO; Non-Final Office Action dated Oct. 21, 2016 in U.S. Appl. No. 14/133,438.
USPTO; Non-Final Office Action dated Jun. 17, 2015 in U.S. Appl. No. 14/542,217.
USPTO; Final Office Action dated Dec. 23, 2015 in U.S. Appl. No. 14/542,217.
USPTO; Notice of Allowance dated Oct. 24, 2016 in U.S. Appl. No. 29/557,960.
USPTO; Final Office Action dated Mar. 21, 2017 in U.S. Appl. No. 14/133,438.

(56) References Cited

OTHER PUBLICATIONS

USPTO; Final Office Action dated Apr. 12, 2017 in U.S. Appl. No. 14/099,803.
USPTO; Advisory Action dated Apr. 25, 2017 in U.S. Appl. No. 14/133,438.

* cited by examiner

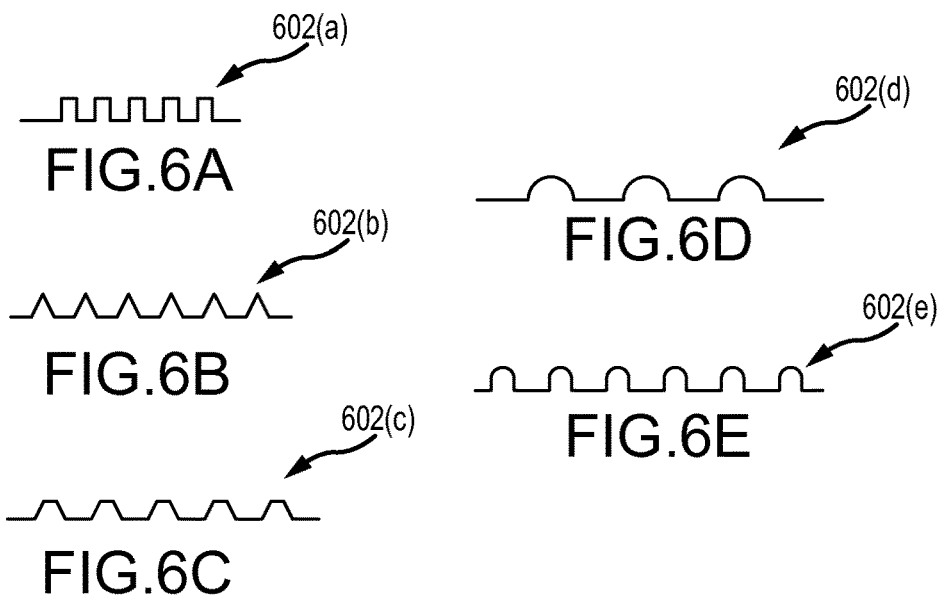
FIG.6A
FIG.6B
FIG.6C
FIG.6D
FIG.6E
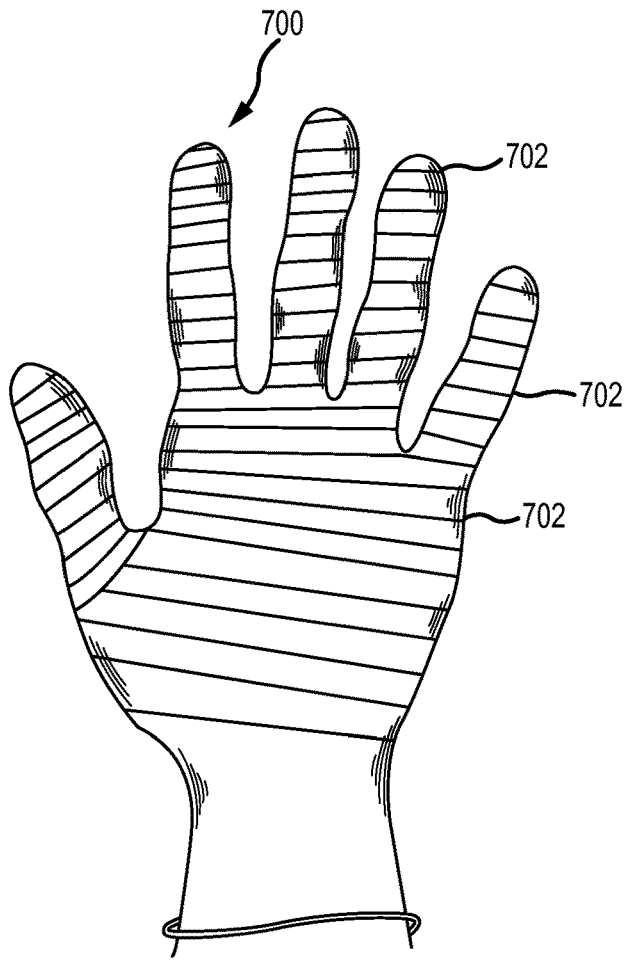
FIG.7

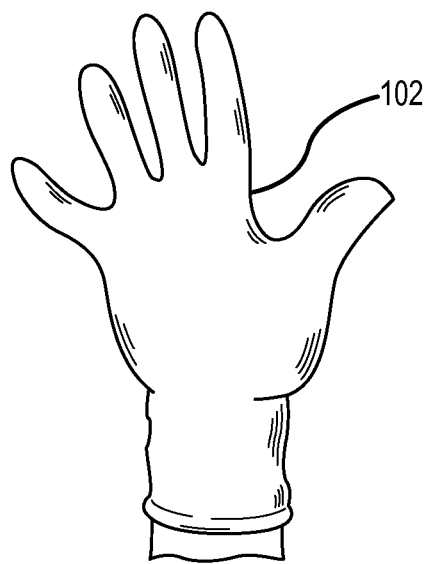
FIG.12
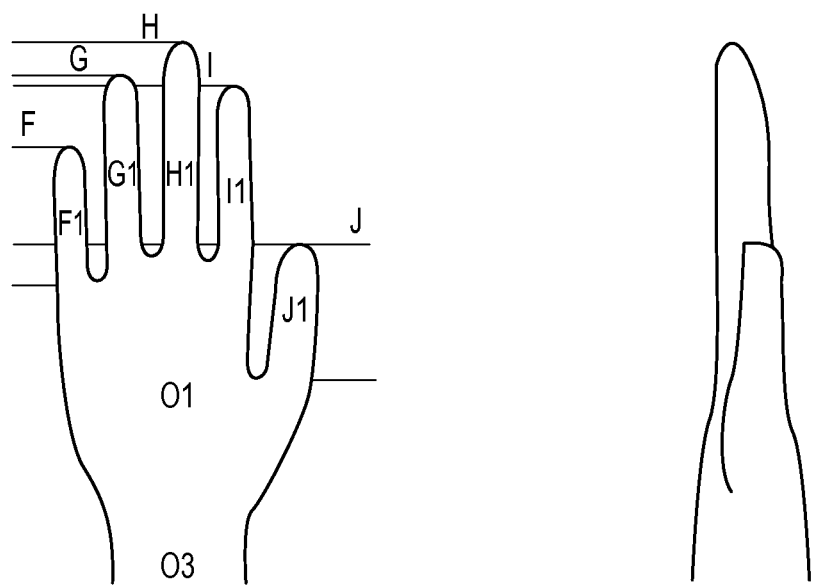
FIG.13A
FIG.13B

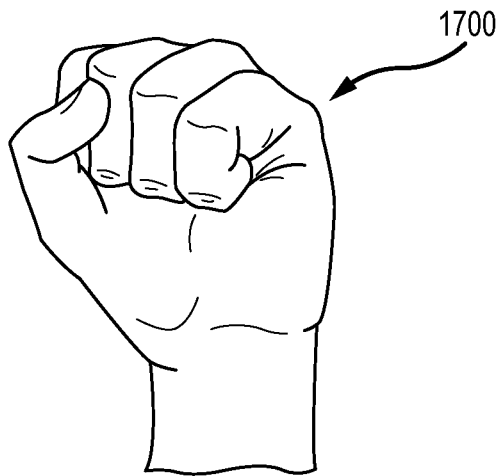
FIG.17
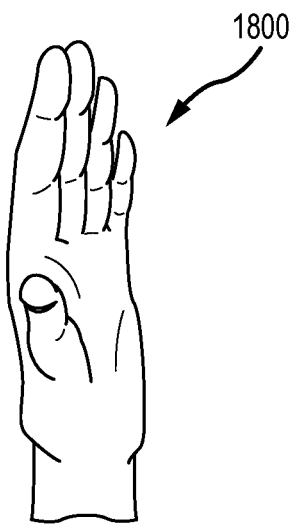 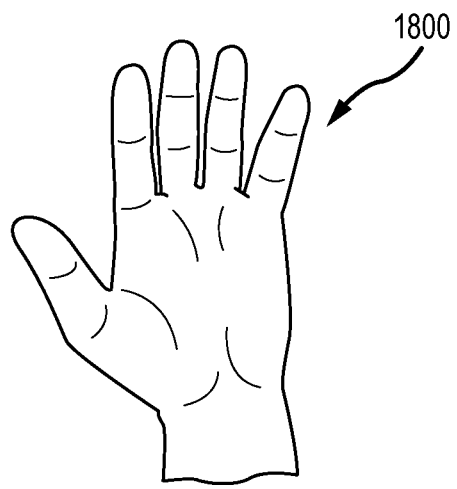
FIG.18A  FIG.18B

SURGICAL GLOVE WITH ERGONOMIC FEATURES

FIELD OF THE INVENTION

The present invention relates to a surgical glove formed to be all or partially in essentially the relaxed shape of a human hand, potentially including being formed in a flexed position at one or more of the finger joints, palm and/or dorsum of the hand. The invention also relates to specific features on the glove to alleviate biasing forces related to movement of the hand and to assist the glove in conforming to the movement of the hand.

BACKGROUND OF THE INVENTION

Surgical gloves are known in the art. The gloves are usually manufactured from latex or latex-free substitutes and fit snugly on the hand. Surgical gloves are often initially formed in a shape approximately the same as a hand when pressed flat on a surface or extended to be essentially flat or straight, such as shown in FIG. 1 and FIG. 2. In that position, the fingers extend outward, essentially straight from the palm (in this context "straight" means there is essentially no bend at any of the joints). In this position, the thumb is oriented in a flat plane or is slightly abducted away from the palm. A problem with the standard glove shape is that the relaxed hand is not naturally in a flat position with the fingers essentially straight. As shown in FIGS. 3-4, when in its normal, relaxed position, which is also called the normal hand cascade position, the joints of the fingers (the fingers and thumb also collectively referred to herein as "digits") are naturally in a flexed position, with the thumb in a different plane than the fingers. This normal position does not match the shape of a standard surgical glove.

If a medical professional wears surgical gloves for a long period, such as when he/she is performing a long procedure or is performing multiple successive procedures in a given period of time, the professional's fingers and hands can become tired or fatigued because of constantly overcoming the biasing forces of the surgical glove(s) in order to flex the fingers and hand (either to a closed position, open position, or both).

Consequently, when a standard surgical glove is placed on a hand, the material of the glove biases the fingers away from the normal, relaxed position to the less natural straight position. When a medical professional then uses his/her hand during a medical procedure, in order to flex the fingers, the biasing force of the glove material must be overcome. For example, FIG. 5 shows a hand 500 of a medical professional grasping a dental instrument 502. Fingers 504-510 are flexed to grasp the instrument 502, and to do so, the biasing force of surgical glove 512 must be overcome. This biasing force is even greater if two gloves are placed on the hand, which is frequently done to increase protection for the medical professional in the event that the outer glove tears or is punctured or if there is a random manufacturing defect resulting in a perforation.

In addition to standard surgical gloves being formed in a straight position, they have no structure to permit the expansion or contraction of the dimensions of portions of the hand. For example, the circumference of a flexed finger (such as when the fingers are flexed towards the palm of the hand) is greater than its circumference when relaxed or in the straight position. This concept is illustrated in FIG. 22, showing a 20% increase in circumference in a female index finger and a 22% increase in circumference in a male index finger. If gloves are designed so they tightly fit fingers that are in the straight position, and then the fingers are flexed, the fingers must also overcome the biasing force of the glove material that restricts digital expansion. Consequently, there is a need for extra material during flexion of the fingers so the portion of the glove covering the portion of the finger that expands can (1) permit expansion when the finger is flexed, and (2) contract back into shape and is not used when the finger is not flexed. The biasing force of gloves also includes adduction of the fingers, a force tending to keep the fingers together in line rather than in their natural cascading position. This is another biasing force that must be overcome when using standard surgical gloves.

Glove designs with baggy, or loose-fitting portions, at one or more areas are known, but such gloves are not optimal for a medical professional performing procedures that require fine, precise work. Glove designs are also known that have ribs at some areas, but while the ribs may help to some degree, they do not overcome the problems described herein.

It would be beneficial for medical professionals to have surgical gloves that minimize biasing forces, that include a minimal amount of excess, loose or baggy material, and that are relatively simple to manufacture, so they are cost effective.

SUMMARY OF THE INVENTION

Aspects of the present invention are surgical gloves (also referred to herein as "gloves") that utilize shapes with the finger portions and thumb positioned more towards their natural, relaxed position. Preferably, the gloves reduce the biasing force inherent in standard gloves when (1) closing the hand, (2) opening the hand, and (3) closing and/or opening the fingers and/or moving the thumb. As set forth in more detail below, a glove according to the invention may also be combined with, or instead include: (a) relaxing or distressing features (also referred to as "patterns") at one or more positions, (b) thinner portions of material at one or more positions, and/or (c) different materials with different flexibility characteristics at one or more positions.

Exemplary surgical gloves are essentially formed either partially or entirely in the approximate shape of a relaxed hand, examples of which are shown in FIGS. 3 and 4. Because of the glove's shape, the amount of biasing force that must be overcome to flex the fingers, move the thumb, close the hand, and/or move the thumb to a position where it is pressed against one of the fingers is reduced. Medical professionals can therefore utilize the gloves for longer periods without their fingers or hands becoming as tired or fatigued as when using conventional surgical gloves.

A surgical glove according to various embodiments of the invention is formed with pre-formed angles (also referred to herein as "flex angles") at one or more of the metacarpophalangeal (MCP) joints, proximal interphalangeal (PIP) joints and distal interphalangeal (DIP) joints in the fingers. Examples of flex angles are shown in FIGS. 3-4. In one example, one or more of the portions of the glove corresponding to the MCP joints may be formed at a flex angle, and/or one or more of the portions of the glove corresponding to the PIP joints may be formed at a flex angle, and/or one or more of the portions of the glove corresponding to the DIP joints may be formed at a flex angle. Any combination or permutation of glove portions corresponding to any combination of joints on any combination of fingers and/or the thumb and/or the palm can include a flex angle as described herein.

In accordance with further examples, MCP joint portions of a glove have a greater flex angle than the PIP and DIP positions to render a glove that more closely replicates the natural, cascading position of the fingers and permits the hand to be in an open, usable position as shown, for example, in FIG. 21.

Additionally, the portion of the glove that retains the thumb may have portions at the thumb MCP and IP joints that are formed at respective flex angles, corresponding to essentially the angle of the relaxed position of the thumb. Further, the overall position of the thumb portion of the glove may be essentially in the thumb's natural, relaxed position, e.g., that of abduction from the palm with some flexion at the MCP and IP joints.

Exemplary gloves can include a texturing or patterning, or other design features, such as patterns, ripples, ribs, textures or bumps, or a combination thereof (collectively, "pattern" or "patterns") formed as part of the glove; such pattern making the glove easier to flex. The patterns provide extra material, which is used when a hand or digit flexes in a certain manner. These patterns can be formed on the outer and/or inner surface of the glove, and are preferably on the outer (or outside) surface.

Patterns can be added to any relevant portion of the glove. As one example, a glove as described herein can include longitudinal ribs along parts of one or more fingers or the thumb to allow for expansion of the digit (i.e., an increase in circumference during flexing). Furthermore, a pattern can exist in one or more spaces between the fingers, or the thumb and index finger, or the thumb and index finger, thus reducing the biasing force of the glove in that area(s) and allowing easier abduction or movement. Also, if the glove is formed with flex angles, it may have a bias toward flexion, rather than extension (the opening of the hand), so features can be added on the palm side of the glove, such as at the thumb, and/or one or more finger creases and/or center of the palm to relieve some of the force of opening or closing the hand and/or digits.

Further, exemplary gloves can include patterns and/or shapes at any suitable location, including at the joint portions including the flex angles. These reduce the biasing force to close and/or open the hand.

In accordance with further exemplary embodiments, a glove may include material of various thicknesses. For example, a glove can include material of a first thickness corresponding to most of the hand, and have material that is thinner at the portions of the hand (which includes the digits) that flex when opening or closing, e.g., at one or more joints of the digits and/or on the dorsum or palm.

In accordance with yet further exemplary embodiments, a glove includes material in some areas that is more flexible in areas where the digits and hand flex, and may include another material that is more puncture resistant than the glove material in other areas. For example, the glove can include reinforced material on the fingertips and/or palm areas and a second material that flexes more at one or more of the joints and/or the dorsum or palm.

Gloves in accordance with the present disclosure can also include any combination of materials, flex angles, patterns, and features as described herein.

As set forth in more detail below, various gloves as described herein can accommodate the movement of the hand and digits with reduced biasing force, and at the same time fit properly (and preferably not be oversized or baggy) throughout the hand's entire range of motion, especially the range used during a medical procedure.

BRIEF DESCRIPTION OF THE DRAWINGS

FIG. 6A is a close-up, side illustration of an exemplary pattern suitable for the material of the glove of FIG. 6.

FIG. 6B is a close-up, side illustration of another exemplary pattern suitable for the material of the glove of FIG. 6.

FIG. 6C is a close-up, side illustration of another exemplary pattern suitable for the material of the glove of FIG. 6.

FIG. 6D is a close-up, side illustration of another exemplary pattern suitable for the material of the glove of FIG. 6.

FIG. 6E is a close-up, side illustration of another pattern suitable for the material of the glove of FIG. 6.

FIG. 7 depicts a top view (wherein the flex angles of the joints cannot be readily seen) of an exemplary glove that includes a pattern of ribs.

FIG. 12 illustrates a hand with a surgical glove wherein the hand is fully extended.

FIG. 13A illustrates a palm view of a standard surgical glove.

FIG. 13B illustrates a side view of the glove of FIG. 13A.

FIG. 17 illustrates a hand without a surgical glove, wherein the hand is fully biased to the flexion position.

FIG. 18A illustrates a side view of a hand in the straight position, which is the position in which most current surgical gloves are formed.

FIG. 18B illustrates a palm view of the hand of FIG. 18A.

DETAILED DESCRIPTION OF PREFERRED EMBODIMENTS

Figure 1:
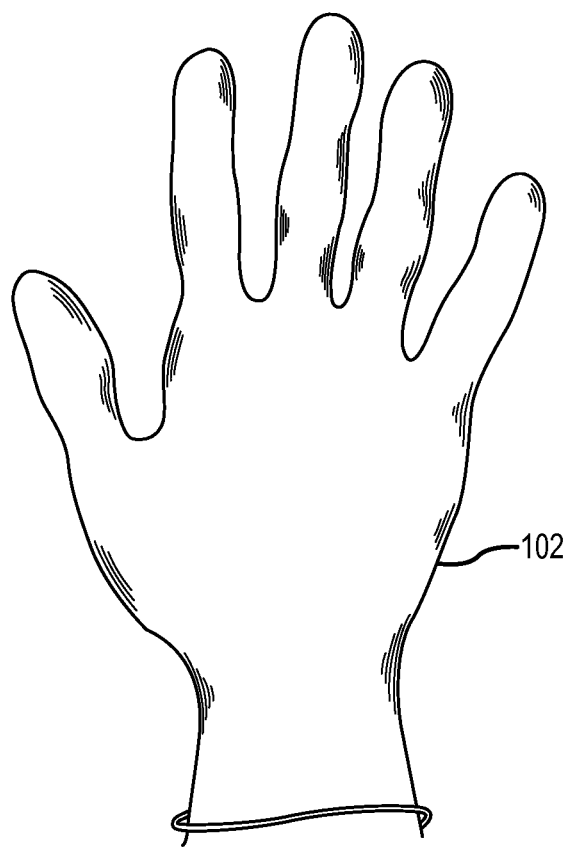
FIG. 1 depicts a hand that is flat with the fingers extending outward from the palm in essentially a straight position, with a surgical glove on the hand.
Figure 2:
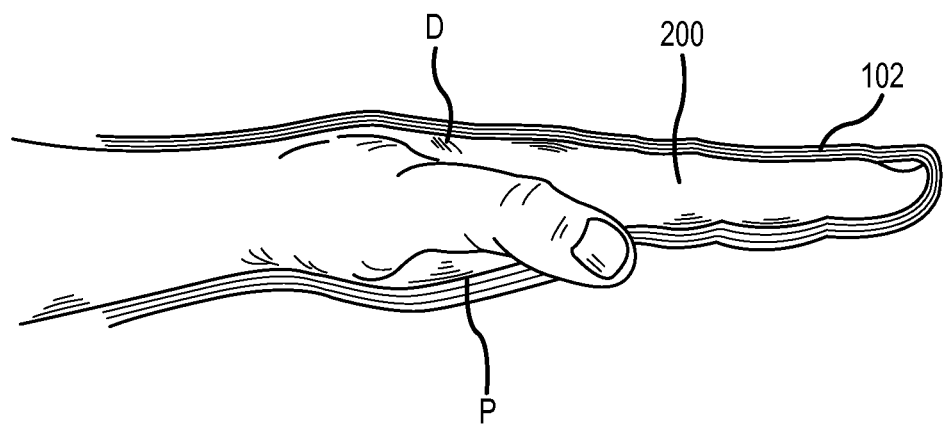
FIG. 2 depicts a partial cross-sectional view of the surgical glove of FIG. 1.
Figure 3:
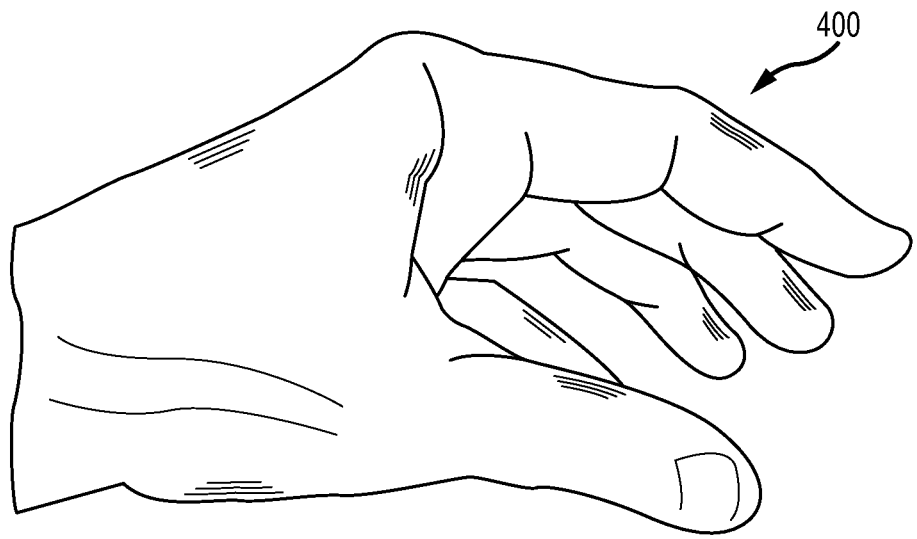
FIG. 3 depicts a hand in a suspended, normal relaxed position and not resting on a surface.

Turning now to the drawings where the purpose is to describe exemplary embodiments of the invention and not to limit the same, FIG. 1 illustrates a top view, FIG. 2 illustrates a side view, and FIG. 12 illustrates a bottom or palm view of a hand 200 in a relatively flat position with a surgical glove 102 thereon. A shape of a conventional glove is further illustrated in FIGS. 13(a) and 13(b), which illustrate a palm view and a side view of the conventional glove.

Figure 20:
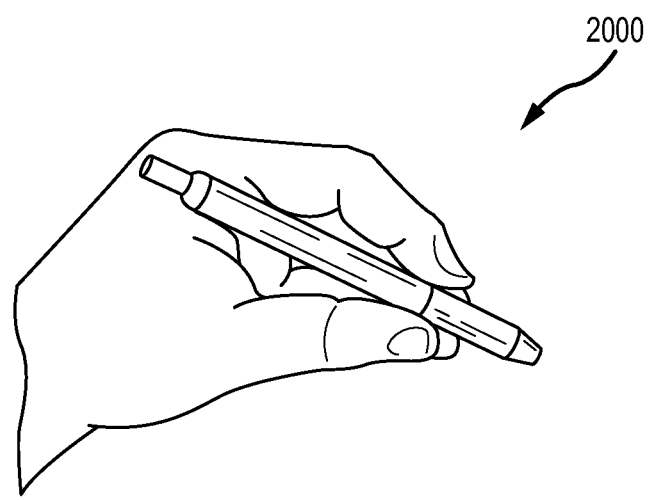
FIG. 20 illustrates a hand in a working position.

To facilitate understanding of the gloves described herein, various hand positions are illustrated in FIGS. 17-21. FIG. 17 illustrates a hand 1700 biased to flexion. FIG. 18A illustrates a side view of a hand 1800 in the straight position, which is the position in which standard surgical gloves are formed. FIG. 18B illustrates a palm view of hand 1800. FIG. 19A illustrates a side, perspective view of a hand 1900 in a fully relaxed position and having cascading fingers. FIG. 19B illustrates a front view of the hand 1900. FIG. 20 illustrates a hand 2000 in a working position.

As is known, an MCP joint is a metacarpophalangeal joint. A PIP joint is a proximal interphalangeal joint. A DIP joint is a distal interphalangeal joint. An IP joint is an interphalangeal joint. And, a CMC joint is a carpometacarpal joint.

A thumb generally includes three joints. The most proximal thumb joint is the CMC joint between the trapezium and the thumb metacarpal. The thumb MCP joint is between the metacarpal and the proximal phalanx of the thumb. The distal most thumb joint is the IP or interphalangeal between the proximal and distal phalanges of the thumb.

Each finger, including the index, middle, ring and little fingers, has four joints including the CMC, MCP, PIP and DIP joints. The CMC joint of each finger is between the metacarpal and the carpal bone. The MCP joint of each finger is between the metacarpal and the proximal phalanx. The PIP joint of each finger is between the proximal and middle phalanges. The DIP joint of each finger is between the middle and distal phalanges.

Figure 4:
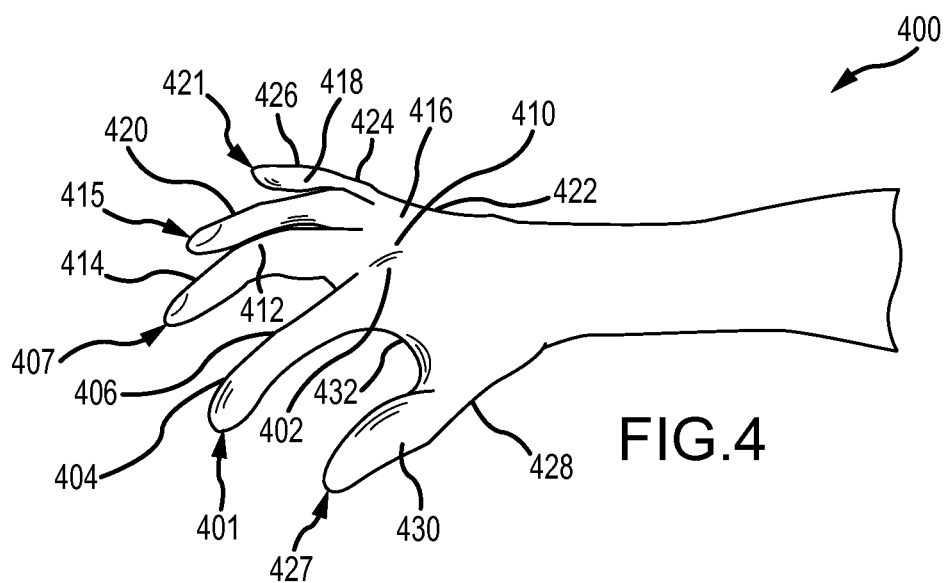
FIG. 4 illustrates a hand in a normal, relaxed position.
Figure 5:
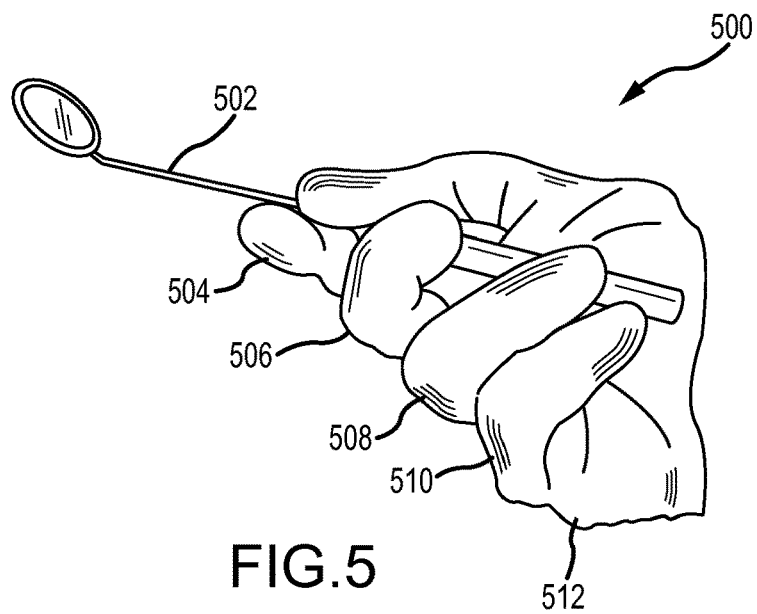
FIG. 5 depicts a hand with a conventional surgical glove thereon, wherein the hand is grasping a dental instrument.

Turning to FIG. 4, respective portions of a hand 400 are shown. Index finger 401 has MCP joint 402, DIP joint 404, and PIP joint 406. Middle finger 407 has MCP joint 410, PIP joint 412, and DIP joint 414. Ring finger 415 has MCP joint 416, PIP joint 418 and DIP joint 420. Little finger 421 has MCP joint 422, PIP joint 424 and DIP joint 426. Thumb 427 has MCP joint 428 and IP joint 430. There is a space 432 between the thumb 427 and index finger 401. Not readily visible are the CMC joints of the fingers and thumb.

Surgical gloves as described herein can be formed of any suitable material, such as medical-grade natural rubber latex or synthetic rubber material. Exemplary synthetic rubber materials include polychloroprene (neoprene), polyisoprene, styrene butadiene, styrene ethylene butadiene. Other suitable materials include nitrile and vinyl (polyvinylchloride). The thickness of the glove material may be any suitable amount and can range between, as an example, 0.14 mm-0.3 mm, and surgical glove thicknesses are known in the art. Surgical gloves come in different sizes, with typical sizes ranging from 5½ to 9, which is also known in the art.

Figure 14:
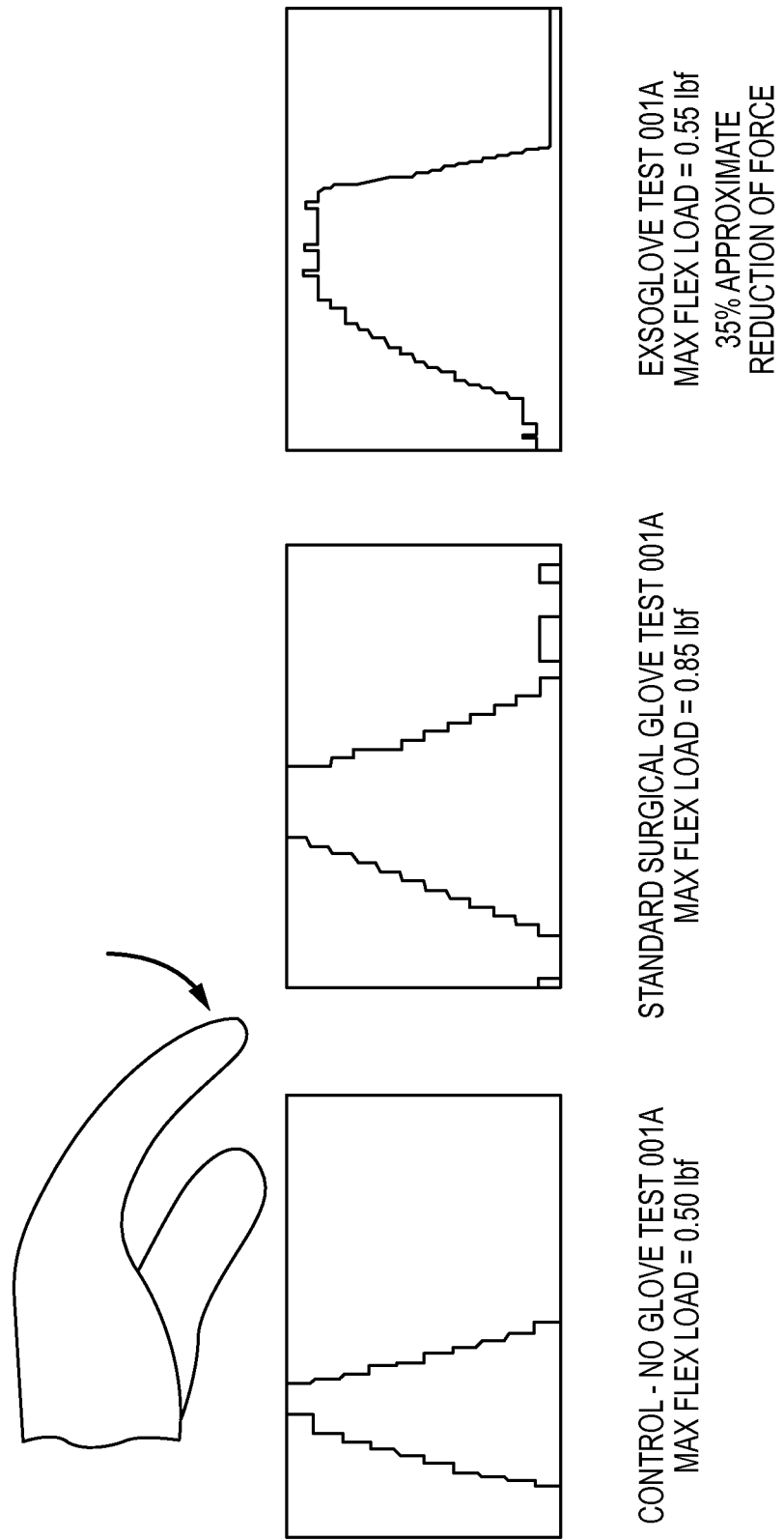
FIG. 14 illustrates comparative strain forces of fingers moving from the straight to the flexed position for various gloves.

Various embodiments of the glove designs described herein can be used alone or in any combination with the other designs and features noted herein. As noted herein, various advantages of the gloves herein described include a reduction of a biasing forces when the hand is opened and/or closed. FIG. 14 illustrates an exemplary reduction in flex load, compared to standard gloves. In this specific illustrated example, gloves in accordance with the present description reduced a flex load by about 35%, although the invention is not limited to this amount.

When referring to a location on a glove according to the invention, it may simply be referenced by the position on the hand (e.g., MCP joint of the index finger) or as a "location," "portion," or "position" or "location of the glove," "portion of the glove," or "position of the glove."

Flex Angles

Figure 21:
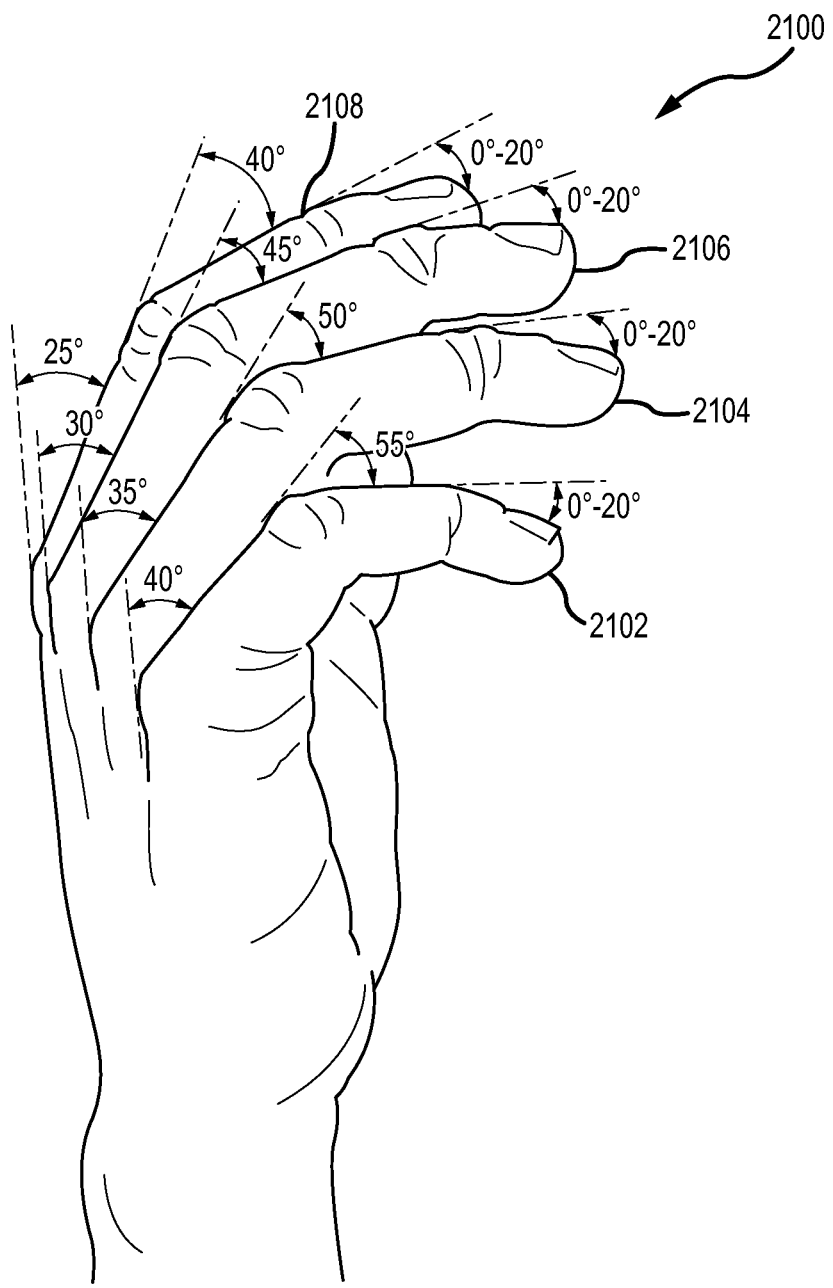
FIG. 21 illustrates a hand in a more natural position, but not the fully relaxed position, and shows the angles of the finger joints when in this position.

Exemplary gloves according to various embodiments of the invention are formed so the portions of the gloves corresponding to the fingers and/or thumb of a hand are more generally in a normal, relaxed hand position, but not entirely in the relaxed position, such as the position illustrated in FIG. 21. In this manner the hand can be closed and opened with limited resisting biasing forces on one or more of the digits and/or hand caused by the glove. By way of examples, portions of a glove corresponding to one or more of the MCP joints, one or more of the PIP joints and/or one or more of the DIP joints of a hand can be formed at a flex angle. A surgical glove according to exemplary embodiments the invention preferably includes one or more of the following portions formed as follows: (a) the portion corresponding to the MCP joint of the index finger is formed at a flex angle of 10-45°, or 40°-50° (b) the portion corresponding to the MCP joint of the middle finger is formed at a flex angle of 10-45°, or 40°-50° (c) the portion corresponding to the MCP joint of the ring finger is formed at a flex angle of 15-50°, or 40°-50°, and (d) the portion corresponding to the MCP of the little finger formed at a flex angle of 20-55°, or 40°-50°.

Further, the following portions of the glove may be formed as follows: (a) the portion corresponding to the PIP joint of the index finger is formed at a 5-45°, or 10°-20°, flex angle, (b) the portion corresponding to the PIP joint of the middle finger is formed at a 5-50° or 10°-20°, flex angle, (c) the portion corresponding to the PIP joint of the ring finger is formed at a 10-55° or 10°-20°, flex angle, and (d) the portion corresponding to the PIP joint of the little finger is formed at a 15-60°, or 10°-20°, flex angle.

Also, (a) the DIP joint of the index finger may be formed at a 5°-25°, or 10°-20°, or 0°-20°, flex angle, (b) the DIP joint of the middle finger may be formed at a 5°-25°, or 10°-20°, or 0°-20°, flex angle, (c) the DIP joint of the ring finger may be formed at a 10°-30°, or 10°-20°, or 0°-20°, flex angle, and (d) the DIP joint of the little finger is formed at a 15°-30°, or 10°-20°, or 0°-20°, flex angle.

Additionally or alternatively, one or more of the following portions of a glove corresponding to the thumb may be formed as follows: (a) the portion corresponding to the MCP joint of the thumb is formed at a flexed angle of 10-45°, and (b) the portion corresponding to the IP joint of the thumb is formed at a flexed angle of 20-50°.

Additionally, gloves according to various exemplary embodiments of the invention can include a two-radius curve, meaning that the angles of the MCP joints are flexed at a greater angle than the other joints.

In one embodiment, the portions of the glove corresponding to the MCP joints have greater flex angles than either the PIP and DIP joints, such that the fingers in the hand remain open to some degree, rather than being in their fully relaxed position. One embodiment of preferred flex angles are approximately:

|  | Index finger | Middle finger | Ring finger | Little finger |
| --- | --- | --- | --- | --- |
| MCP joint | 25° | 25° | 30° | 35° |
| PIP joint | 15° | 15° | 20° | 25° |
| DIP joint | 15° | 15° | 20° | 25° |

Although these angles are less than the complete relaxed position of the hand, they allow for: ease of manufacturing, helping to keep the hand open to some degree, and preventing too much bias against opening or closing the hand.

Any of the flex angles set forth herein could possibly be varied beyond the stated ranges to better approximate the shape of a hand in a position to reduce biasing forces when the hand opens or closes.

Another aspect of the invention is that when in a relaxed position, the fingers may be in a cascading position moving from the index finger to the little finger, with the flex angles of the joints of each finger varying. An example of a hand 2100 including cascading fingers 2102-2108 is illustrated in FIG. 21. Some embodiments of the gloves disclosed herein include this cascading feature. One way in which a glove according to the invention compensates for this cascading position is by providing different flex angles, or features to permit flexing, at the various joints. Exemplary angles for the cascading digits are illustrated in FIG. 21, and these angles may fall within ranges as set forth in the exemplary embodiments herein.

Additionally, the palm region of the glove may be formed at a suitable flex angle, such as between 10°-30°. Moreover, a glove according to the invention may have the thumb portion formed in a more natural position with the thumb in a different plane than the fingers.

Figure 25A:
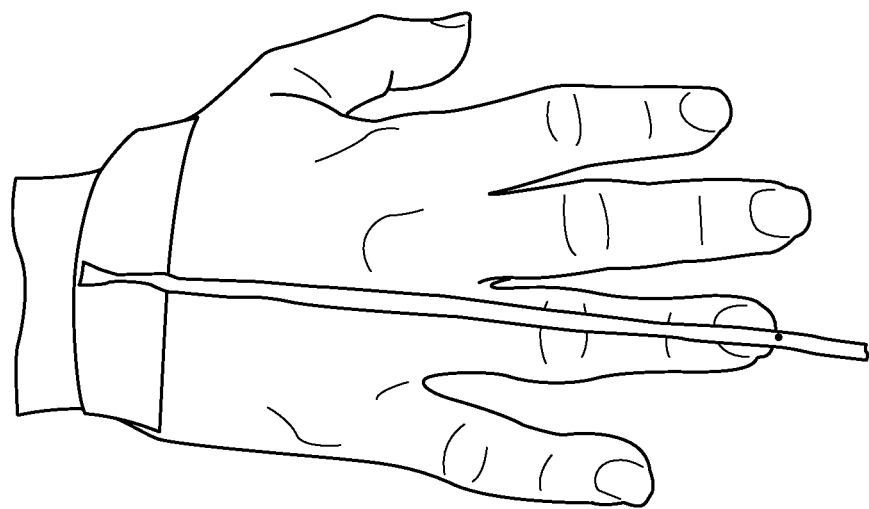
FIG. 25A illustrates the hand in a flat position with the figures extended.
Figure 25B:
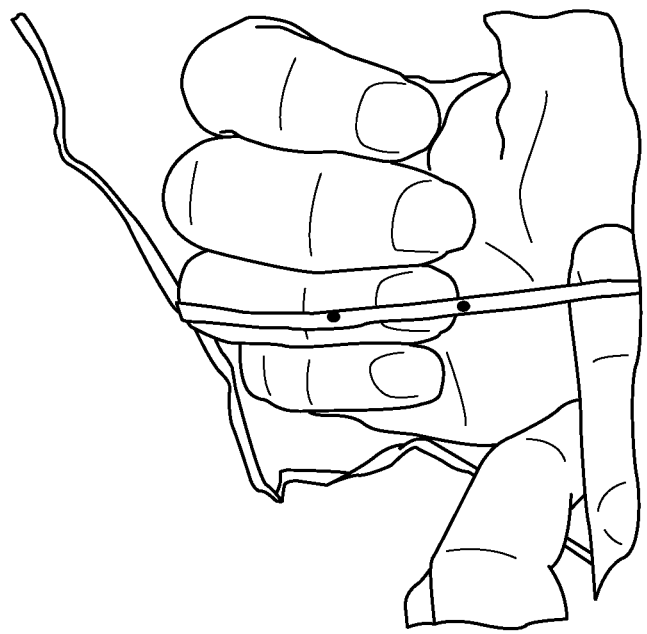
FIG. 25B illustrates the hand of FIG. 25A with the fingers flexed to essentially a fully-closed position.

When the fingers are flexed from an extend to a closed position, as illustrated in FIGS. 25A-25B, the length along the top of the finger, measured from a position just behind the MCP joint of the finger increases. For a size 6.5 glove and 8.0 glove, the length along the top of each finger increases by approximately the amounts shown below:

|  | Index finger | Middle finger | Ring finger | Little finger |
| --- | --- | --- | --- | --- |
| Size 6.5 glove | 10 mm | 13 mm | 20 mm | 32 mm |
| Size 8.0 glove | 11 mm | 15 mm | 24 mm | 30 mm |

The difference in increased length moving from the index finger to the little finger is because of the cascading shape of the hand when relaxed or closed.

Figure 26:
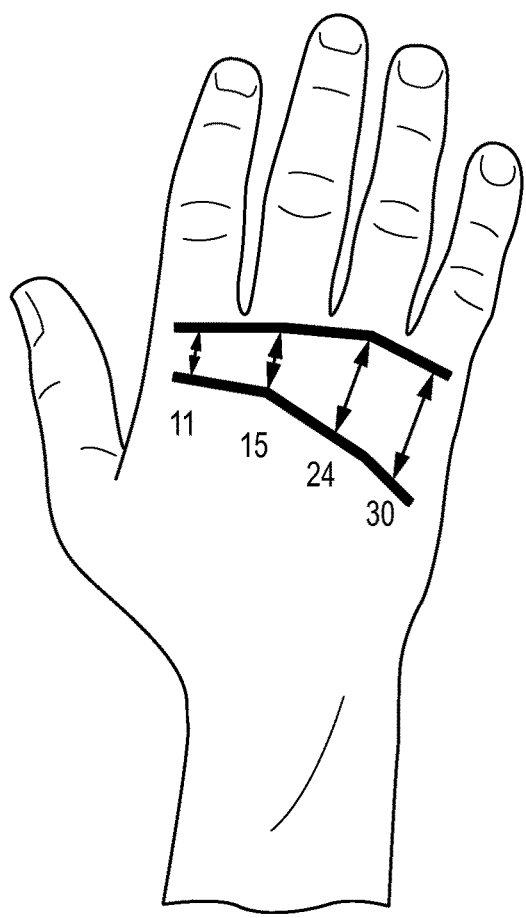
FIG. 26 is a top view of a hand illustrating the amount of extra material or stretch (as measured from the MCP joints) for the fingers to move from a straight to a cascading position for a size 8 glove.
Figure 27:
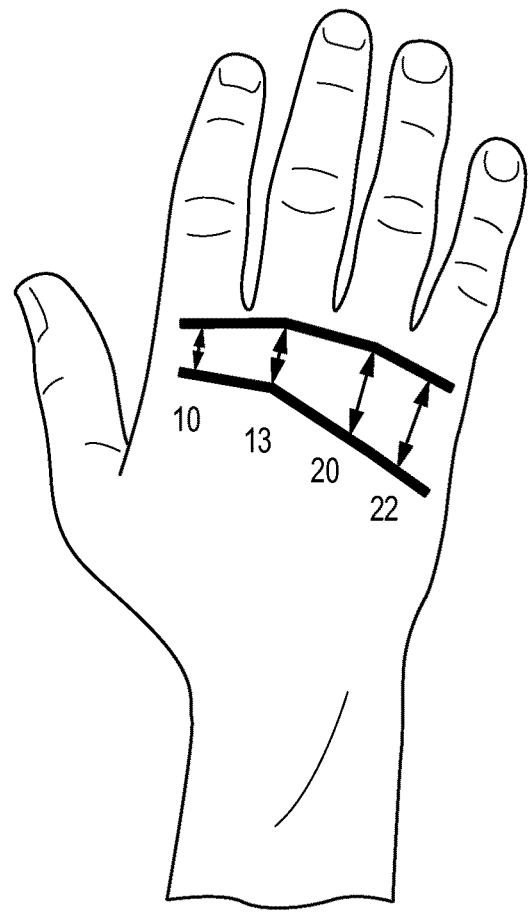
FIG. 27 illustrates the amount of extra material or stretch (as measured from the MCP joints) for the fingers to move from a straight to a cascading position for a size 6.5 glove.

Therefore, it is desirable to provide extra material for the tops of the fingers (and thumb) when in the closed position to reduce biasing forces. This can be done by pre-flexing the glove as described herein so it is formed in a position that is close to, but preferably not quite, in the position of a relaxed hand and/or by including patterns. In one embodiment corresponding to the above chart, all of the extra material is provided at the MCP joint of each finger, as illustrated in FIG. 26 (for a size 8.0 glove) and 27 (for a size 6.5 glove). The extra material is preferably (a) half provided by the flex angles for the MCP joints disclosed herein, and (b) half provided by patterns (discussed below). Alternatively, the extra material may be entirely provided by flex angles at two or more joints of a finger, or by flex angles at two or more joints of each finger and patterns at one or more joints of each finger.

Figure 28C:
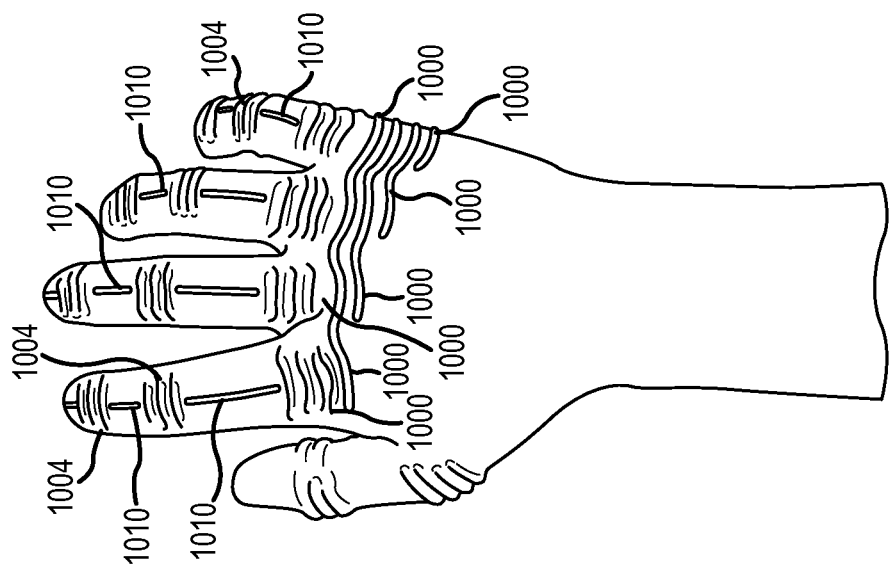
FIG. 28C is a top view of the glove of FIG. 28A.
Figure 28B:
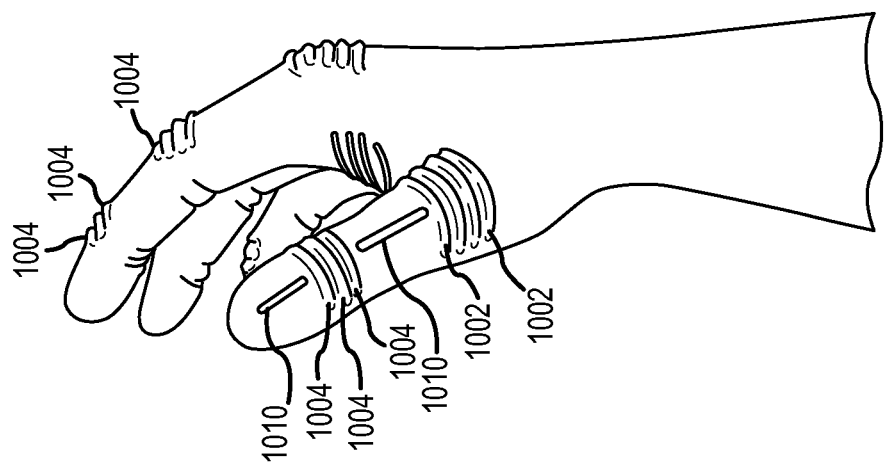
FIG. 28B is a side view of the glove of FIG. 28A.
Figure 28A:
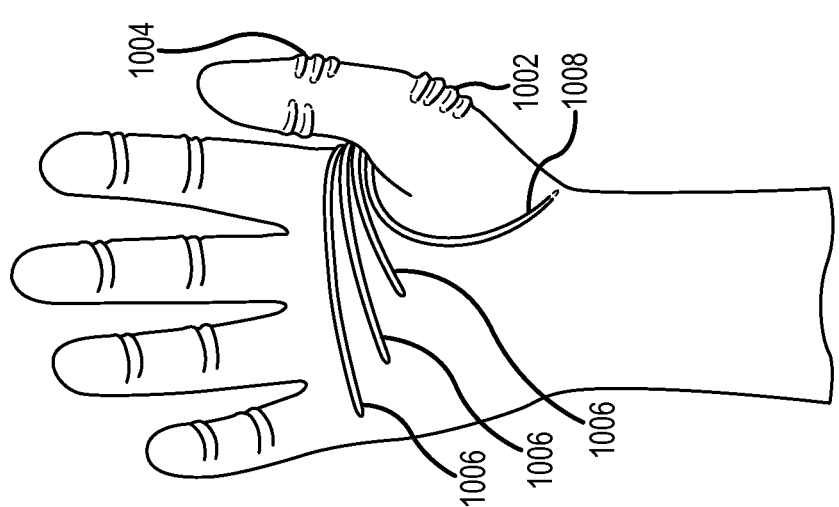
FIG. 28A is a palm view of a glove in accordance with an embodiment of the invention.
Figure 29:
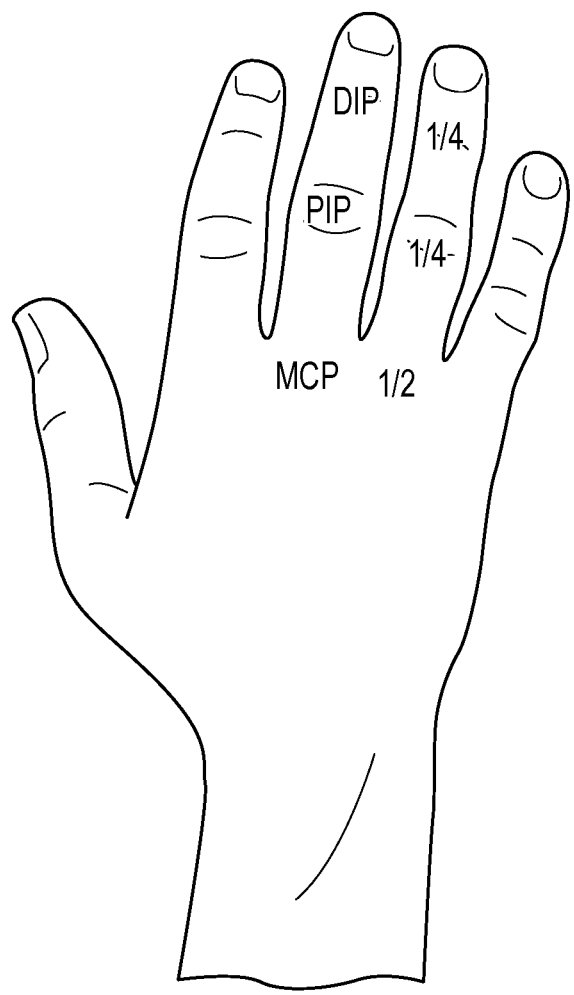
FIG. 29 is a top view of a hand.

FIGS. 28A-28C show a glove in accordance with the invention wherein approximately ½ of the extra material required along the top side of the finger when fully flexed is provided by flex angles at each finger joint and about half is provided by patterns, which are preferably ribs at each joint. As shown in FIG. 29, in one embodiment, about ½ of the extra length required for fully closing each finger is provided at the MCP joint, about ¼ is provided at the PIP joint and about ¼ is provided at the DIP joint.

Patterns

Figure 6:
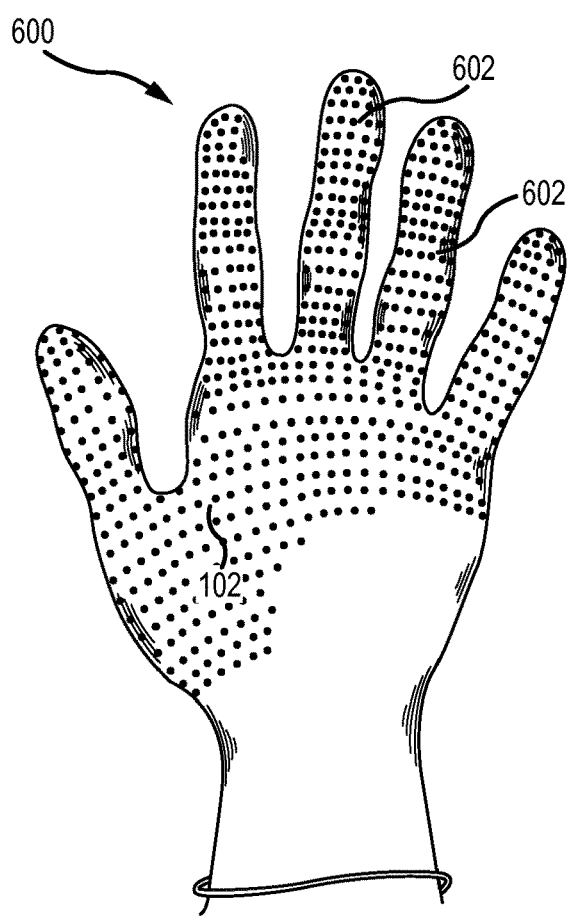
FIG. 6 depicts a top view (wherein the flexed angles of the joints cannot be readily seen) of an exemplary glove that includes a pattern.

A glove according to the exemplary embodiments of the invention can additionally or alternatively have a pattern formed therein at various positions that allows easier flexing of the glove material. Some exemplary patterns are shown in FIGS. 6-6E and each provides additional material for opening and/or closing the hand to reduce biasing forces when stretched, and reduce or eliminate a baggy fit when not stretched. The pattern may be one or more of the following:

(1) Any feature with about 10 mm or less of total height or depth that permits a glove to flex with less force when the hand is opened, closed or both.

(2) The material forming the glove may be ribbed, wherein the ribs (which are folds of material) include excess material to permit expansion of the glove and the ribs may extend about ⅛" or less beyond the outer surface of the glove on either the dorsum side, palm side, between the fingers, between the thumb and fingers, or some combination thereof. FIG. 2 illustrates a dorsum D side of hand 200 and a palm side P of hand 200.

(3) The material forming the glove can have a pattern of (e.g., alternating) raised portions and/or depressions, wherein the center of each raised portion or depression is preferably no greater than ¼" inches apart from other portions, and most preferably no greater than ⅛" to 1/32" apart. The raised or depressed portions are preferably formed in one or more of cross-sectional shapes from the group consisting of: semi-oval, semi-circle, square, rectangular, triangular, three-sided pyramidal and four-sided pyramidal. The pattern may follow the natural contour of the hand where desired. This can create nonlinear and asymmetrical patterns.

A glove can include a more concentrated pattern of patterns proximate areas corresponding to areas of the digits and hand that bend or stretch, thereby allowing easier bending at the areas that need to bend more, such as at one or more of the MCP, PIP, DIP, or IP joints, or in area 32 between the thumb and index finger, or in the web spaces between the other fingers. As another example, a pattern may be present and/or more concentrated along the axis of the dorsum of the little finger, or be more concentrated from the mid hand to the mid proximal phalanx. Or, the pattern may cover any portion of the dorsum or palm. On the index finger, the pattern may cover the distal hand to the proximal phalanx. The pattern may be biased toward the ulnar side of the hand where biasing forces are greatest. On the thumb MCP joint, the pattern may predominate on the dorsum, but might extend into area 32. Additionally, the pattern may be placed along the longitudinal axis of one or more of the fingers and/or thumb.

A glove including a pattern might include the same pattern or different patterns, such as one pattern at one or more of the joints, and another between the spaces between the fingers. For example, alternating raised portions or depressions in the form of a four-sided pyramid may be at any suitable location on the gloves, including on part of or the entire palm side of the glove, and there may be ribs running into the spaces between the fingers, or on the flexor surface of the gloves to relieve biasing forces of extending fingers associated with pre-relaxed surgical gloves. The ribs allow easier expansion to decrease the loads on the digits with abduction of the fingers or wide stretching of the hand, in the same fashion as one would need to play far apart piano keys. The glove can include a pattern over or under any of the joints of one or more of the digits. Further, a pattern can be placed in the mid palm to provide some relaxation during maximal extension of the fingers.

Other Exemplary Embodiments

As shown in FIGS. 28A-28C, a glove according to the invention has patterns formed as ribs. In this embodiment ribs 1000 are positioned at the top of each MCP joint and either encircle, or are on the top and palm side, of each PIP joint and DIP joint. The ribs also encircle the thumb PIP and IP joint, and extend along the palm and into the space between the thumb and index finger. There are four separate, non-connected ribs positioned at the thumb PIP joint; four separate, non-connected ribs positioned at the index finger MCP joint, five separate, non-connected ribs at the MCP joint of the middle finger; six separate, non-connected ribs at the MCP joint of the ring finger; and seven separate, non-connected ribs at the MCP joint of the little finger.

In this embodiment, one rib 1000, which is the fourth rib (as measured from the distal ends of the fingers) for each of the index finger, middle finger, ring finger and little finger, is continuous to assist in flexion of the hand between the fingers. Another rib 1000, which is the fifth rib (as measured form the distal ends of the fingers) for each of the middle finger, ring finger and little finger, is continuous to assist in flexing of the hand. Another rib 1000 is the sixth rib (as measured from the distal ends of the fingers) for each of the ring finger and little finger and assists in flexing of the hand. The IP joint of the thumb has four separate, non-connected ribs 1002, and the PIP and DIP joint of each finger has three separate, non-connected ribs 1004.

The ribs in this example have a curved relief at the MCP joints, wherein the end of each rib at an MCP joint is preferably between 1 mm to 3 mm closer to the distal end of the respective finger on which it is positioned than the center of the rib.

There are also three separate, non-connected ribs 1006 in the palm section, wherein the uppermost rib extends under the little finger, the center rib extends to approximately a position between the little finger and ring finger, and the lower rib extends to approximately the ring finger. There is also an additional rib 1008 running along the muscle of the thumb to assist in flexing the thumb towards the palm or fingers.

Additionally, this example has ribs 1010 extending longitudinally between the MCP joint and PIP joint of each finger, the PIP joint and DIP joint of each finger, the PIP joint and the IP joint of the thumb, and distal of the IP joint of the thumb. Each of these ribs can expand by 1 mm to 10 mm.

Patterns according to the invention may provide between 1 mm to 250 mm of extra material depending upon their location on the glove. For example, a pattern positioned at the MCP joint of the: (a) index finger may provide 2 mm to 15 mm, or 2 mm to 11 mm of extra material, (b) the middle finger may provide 3 mm to 20 mm, or 3 mm to 15 mm, of extra material, (c) the ring finger may include 4 mm to 25 mm, or 4 mm to 24 mm, or extra material, and (d) the little finger may include 5 mm to 30 mm, or 5 mm to 35 mm, of extra material. A pattern positioned at the PIP and/or DIP joint of the: (a) index finger may provide 1 mm to 8 mm, or 1 mm to 10 mm, of extra material, (b) middle finger may provide 1 mm to 11 mm, or 2 mm to 10 mm, of extra material, and (c) ring finger may include 2 mm to 13 mm, or 2 mm to 10 mm, or extra material. A pattern positioned at the thumb PIP joint may provide for 5 mm to 20 mm of extra material, and a pattern positioned at the thumb IP joint may provide for 8 mm to 20 mm of extra material.

A pattern positioned between the thumb and index finger may provide 20 mm to 250 mm of extra material and pattern positioned between any two fingers may provide 20 mm to 200 mm of extra material. A pattern on the palm may provide 30 mm to 350 mm of extra material.

Some non-limiting examples of gloves having different patterns are illustrated in FIGS. 6-11. FIG. 6 illustrates a glove 600 having a pattern 602. As illustrated, pattern 602 covers all of the joints of the digits, the space between the thumb and index finger, and the spaces between each finger. Pattern 602, or any suitable pattern used with the gloves described herein, could cover any suitable portion of the glove, such as one or more of: the portion corresponding to one or more joints, the portion corresponding to the space between the thumb and index finger, any or all spaces between the fingers, the dorsum, and the palm.

FIGS. 6A-6E illustrate close up, side views of exemplary structures suitable for pattern 602. FIG. 6A illustrates pattern 602(*a*) as raised square or rectangular sections. FIG. 6B illustrates pattern 602(*b*) as raised triangular sections, which would be pyramidal if viewed in three dimensions. FIG. 6C illustrates pattern 602(2) as raised flat-topped pyramidal sections. FIG. 6D illustrates pattern 602(*d*) as raised broad partial ovoid or partial spherical sections. FIG. 6E illustrates pattern 602(*e*) as raised dome-like sections. Any suitable structures, or combination of structures, however, could be used to form pattern 602.

FIG. 7 illustrates a glove 700 according to various embodiments of the invention with ribs 702 to assist with easier flexing. Exemplary ribs 702 are formed in the material of glove 700 and are preferably no higher than about 2 mm, although any suitable height can be used. The spacing between the ribs may be any suitable spacing and may vary at different areas of the glove. Preferably, the ribs 702 are spaced apart between 1/16" and 1/4."

Figure 8:
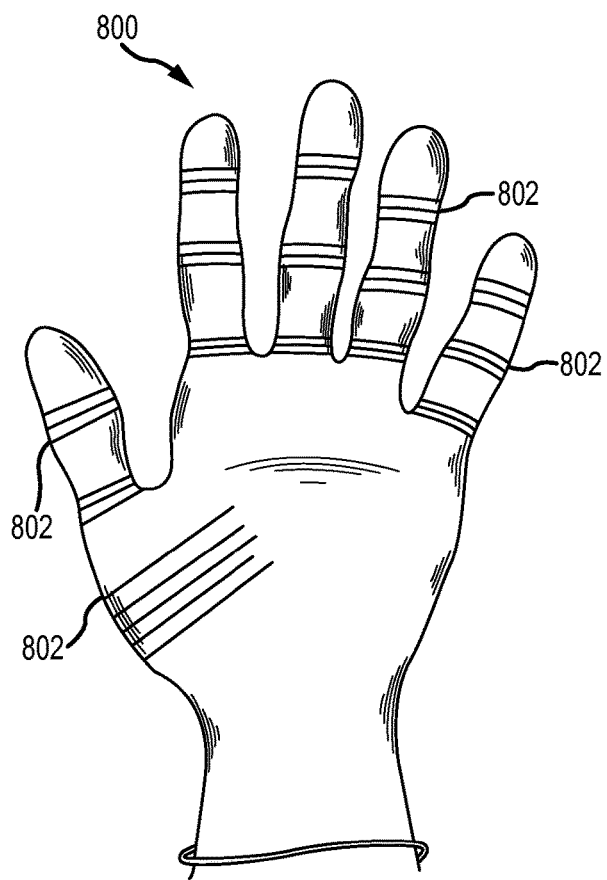
FIG. 8 depicts a top view (wherein the flex angles of the joints cannot be readily seen) of an exemplary glove that includes a pattern of ribs in selected portions of the glove.

FIG. 8 illustrates a glove 800 according to further exemplary embodiments of the invention with ribs 802 to assist with easier flexing. Exemplary ribs 802 can be the same as previously described ribs 702, except ribs 802 only extend along the portions of the glove that correspond to the locations of the joints.

Figure 9:
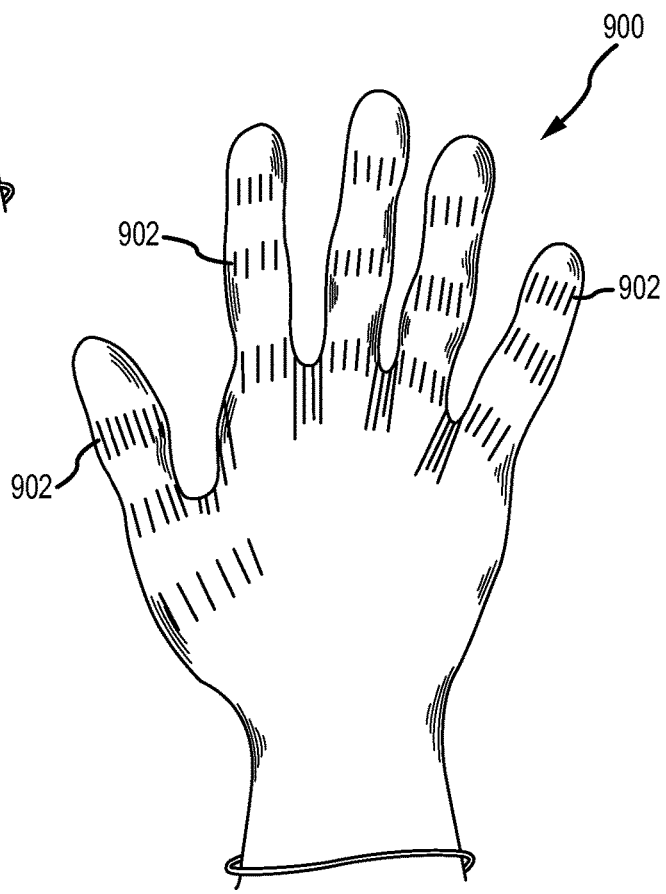
FIG. 9 depicts a top view (wherein the flex angles of the joints cannot be readily seen) of an exemplary glove that includes a pattern of ribs in selected portions of the glove, wherein the ribs are axially oriented to the digits.

FIG. 9 illustrates a glove 900 according to yet further exemplary embodiments of the invention with ribs 902 to assist with easier flexing. Exemplary ribs 902 are formed in the material of glove 900, are axially-aligned along the digits, and are preferably no higher than 2 mm, although any suitable height can be used. The spacing between the ribs may be any suitable spacing and may vary at different areas of the glove. Preferably, the ribs 902 are spaced apart between 1/16" and 1/4."

Figure 10:
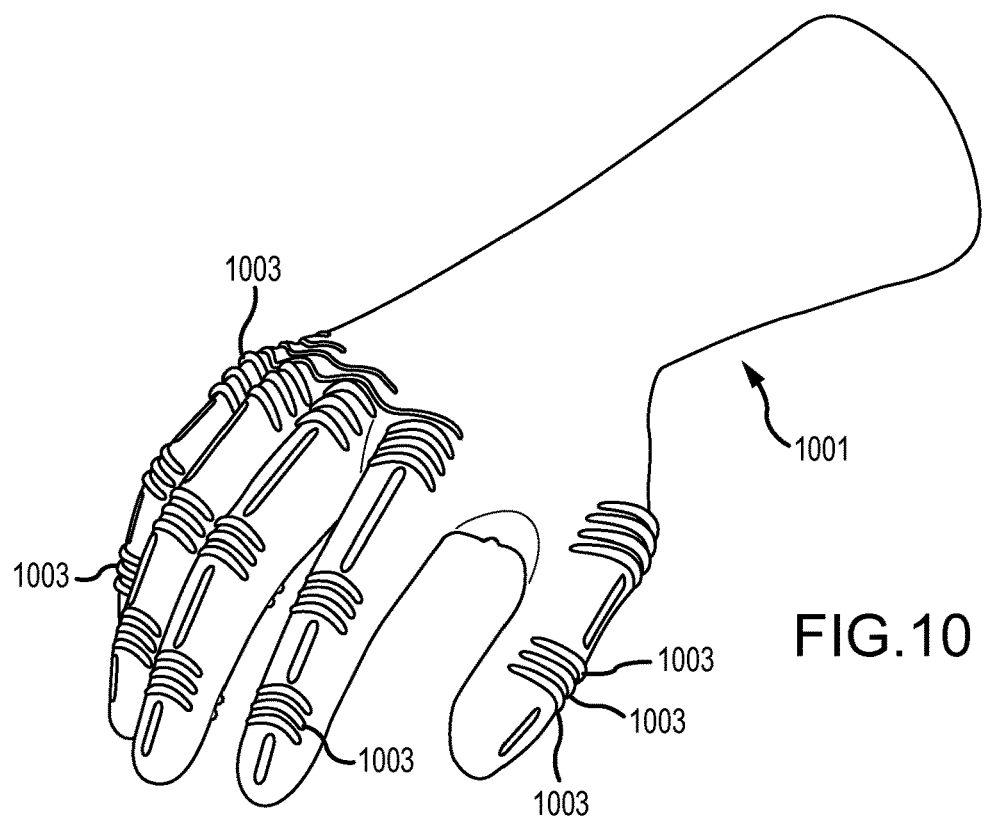
FIG. 10 depicts a top, perspective view of an exemplary glove that includes a pattern of ribs in selected portions of the glove.

FIG. 10 illustrates a glove 1000 according to additional exemplary embodiments of the invention with ribs 1002 to assist with easier flexing. Ribs 1002 are formed in the material of glove 1000 and are preferably no higher than 2 mm, although any suitable height can be used. The spacing between the ribs 1002 may be any suitable spacing and may vary at different areas of the glove. Preferably, the ribs 1002 are spaced apart between 1/16" and 1/4."

Figure 11:
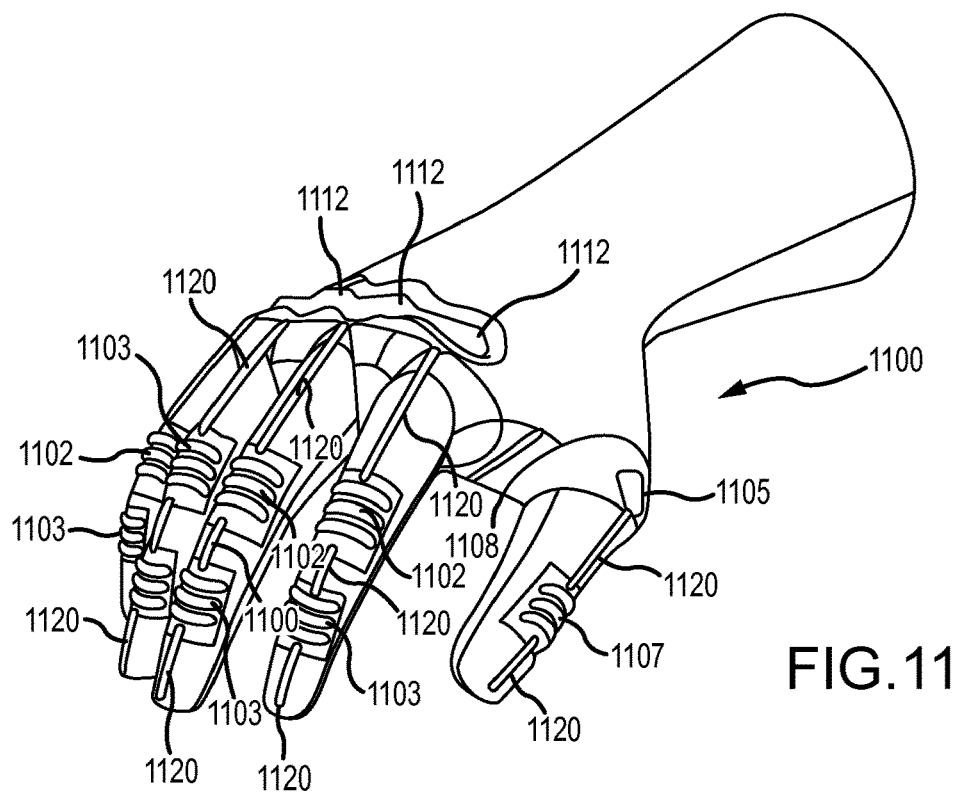
FIG. 11 depicts a top, perspective view of a glove in accordance with an alternate embodiment of the invention.

FIG. 11 illustrates another glove 1100 according to various embodiments of the invention. Glove 1100 includes alternating patterned/textured sections that correspond with the location of each joint separated by non-patterned/non-textured sections that are ribs to provide extra material when the hand or a finger flexes.

These folds of material (ribs) can be located in any suitable place, including between any two joints, between any fingers, between the thumb and index finger, on the dorsum of the hand and/or on the palm of the hand. The folds can provide any suitable amount of material to permit expansion, and in one embodiment provide between 1/16" and 1/4" of extra material. The folds preferably extend outward away from the hand and/or fingers. In the illustrated example, glove 1100 includes a flexible section 1112 corresponding to the MCP of each finger, a flexible section 1102 corresponding to the PIP of each finger, and a flexible section 1103 corresponding to the DIP of each finger. There is a flexible section 1105 corresponding to the MCP of the thumb and a flexible section 1107 corresponding to the IP of the thumb. There is also a longitudinally oriented pattern 1120 between each of the flexible sections and distal from the DIP joints and IP joint that allows for circumferential expansion of the gloves to minimize biasing forces associated with natural digital circumferential expansion that occurs with normal digital flexion.

Figure 15:
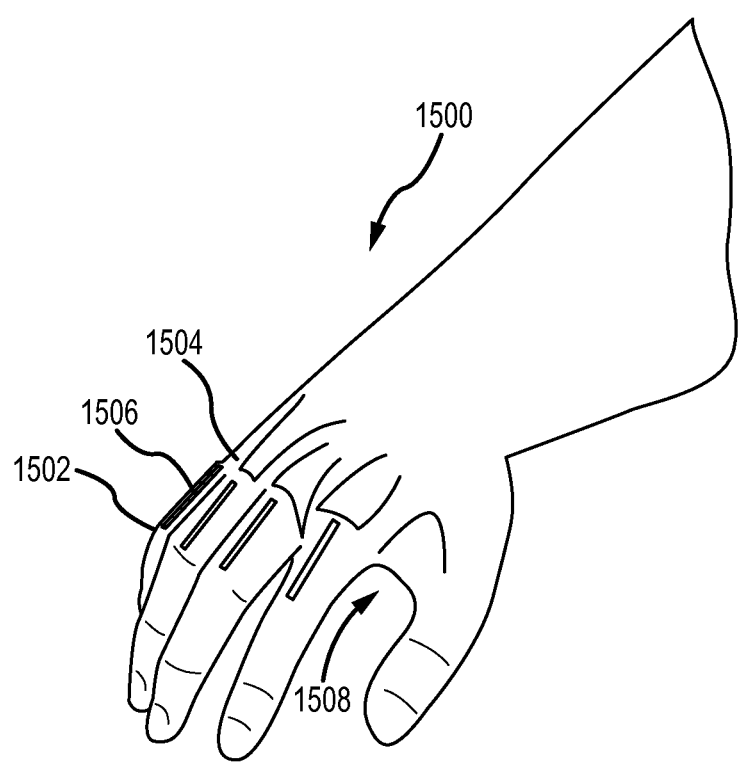
FIG. 15 illustrate another glove having a pattern in accordance with additional embodiments of the invention.
Figure 16B:
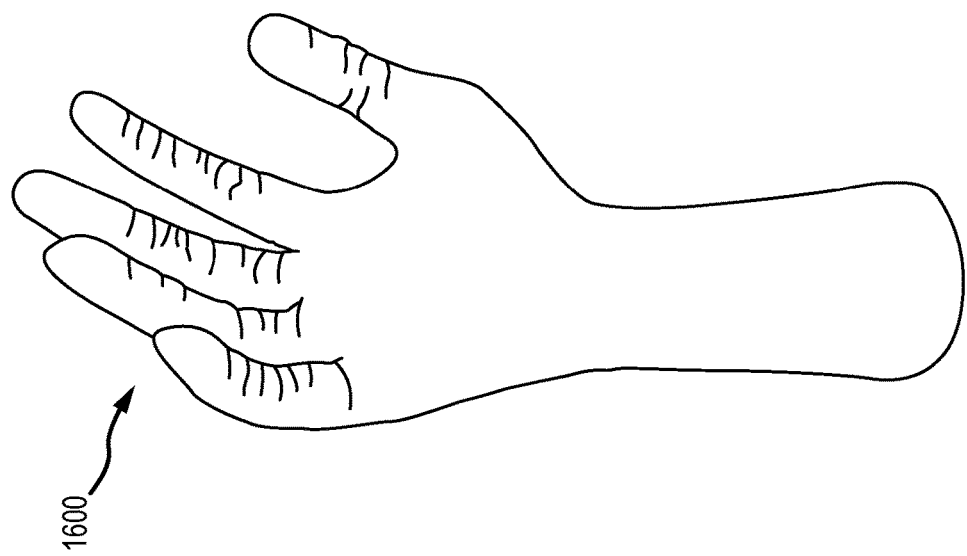
FIGS. 16(a) and 16(b) illustrate another glove having a pattern in accordance with additional embodiments of the invention.
Figure 16A:
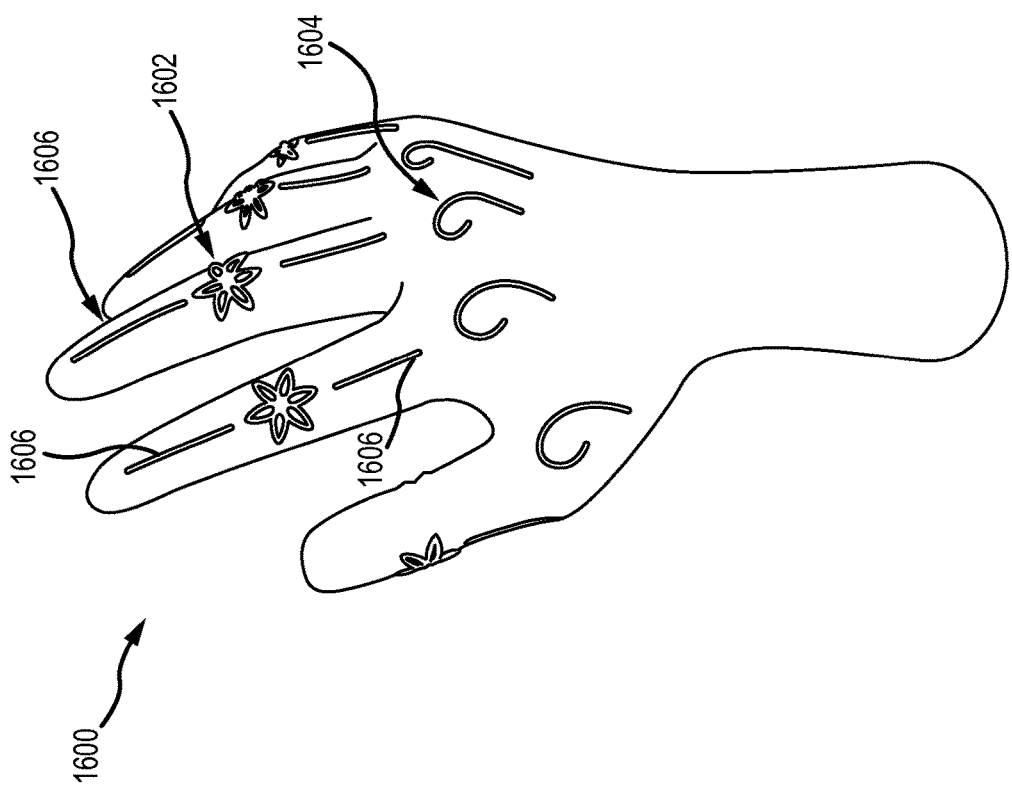
Figures 19A, 19B:
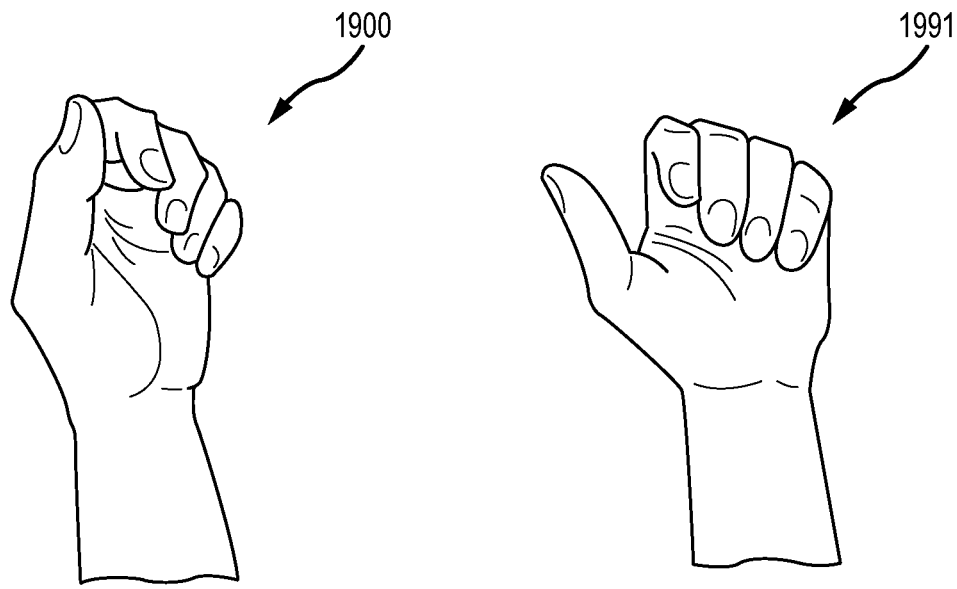
FIG. 19A illustrates a side, perspective view of a hand in a fully relaxed position.
FIG. 19B illustrates a front view of the hand in FIG. 19A.

FIGS. 15 and 16(*a*) and (*b*) illustrate additional exemplary gloves 1500 and 1600, respectively. Glove 1500 includes PIP joint modifiers 1502, MCP expansion ridges 1504, a proximal expansion groove 1506, and palm expansion channels 1508 in accordance with exemplary embodiments of the invention.

Glove 1600 includes joint strain relief elements 1602, 1604 and longitudinal expansion relief ridges 1606. Strain relief elements 1602, 1604 can be of any suitable shape that provides a desired amount of stain relief—e.g., greater than or equal to 5%, 10%, 25%, 35%, 50%, or the like. As illustrated, elements 1602, 1604 can be decorative, as long as they provide the desired relief of biasing forces. Similarly, ridges 1606 can provide a desired amount of expansion relief, such as greater than or equal to 5%, 10%, 25%, 35%, 50%, or the like.

Figure 22:
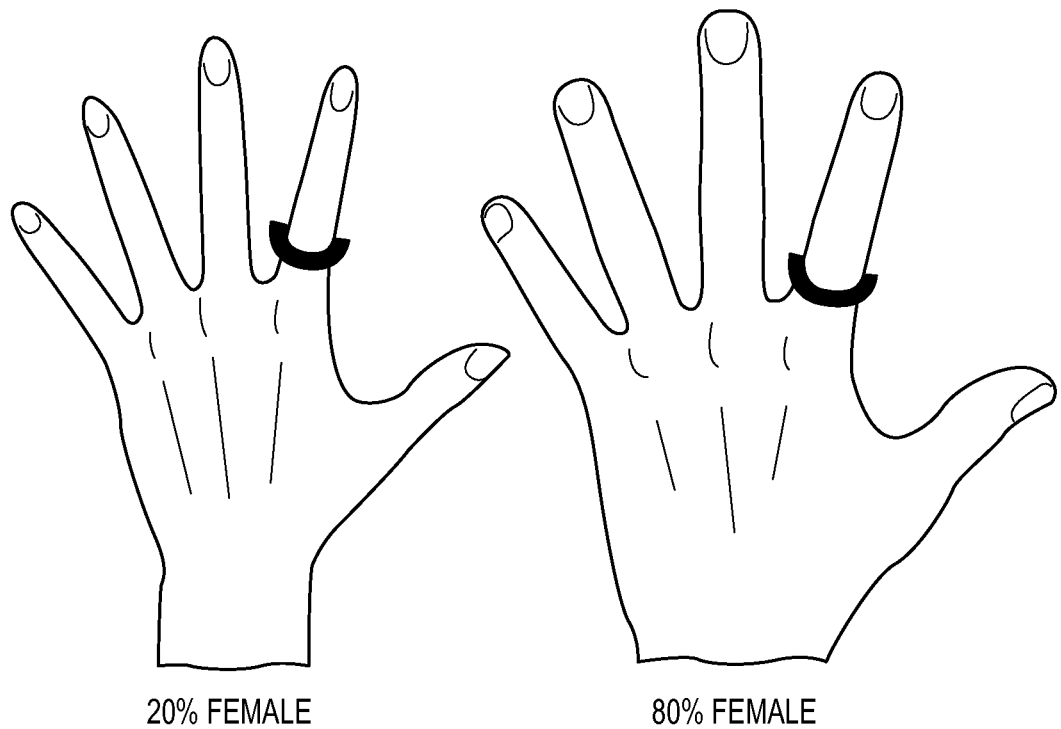
FIG. 22 illustrates a relationship between the circumference of fingers when straight and when flexed.

As previously mentioned, it is also preferred that a glove according to the invention be able to compensate for the expansion of the fingers' respective circumferences when flexed. FIG. 22 illustrates a relationship between the circumferences of fingers when straight and when flexed. A digit circumference can increase from about 15% to about 25% from an extended position to a flex position.

Figure 23:
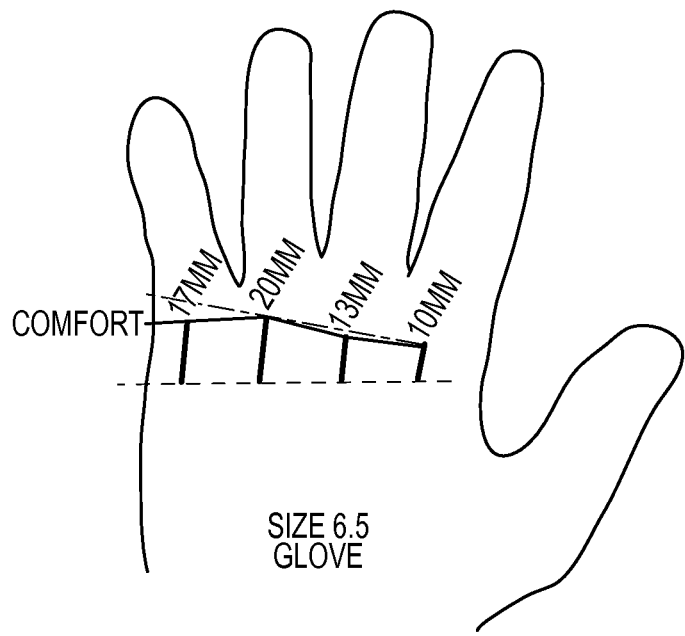
FIG. 23 illustrates an amount of stretch and location of the stretch for a size 6.5 glove at the MCP joints of the fingers.
Figure 24:
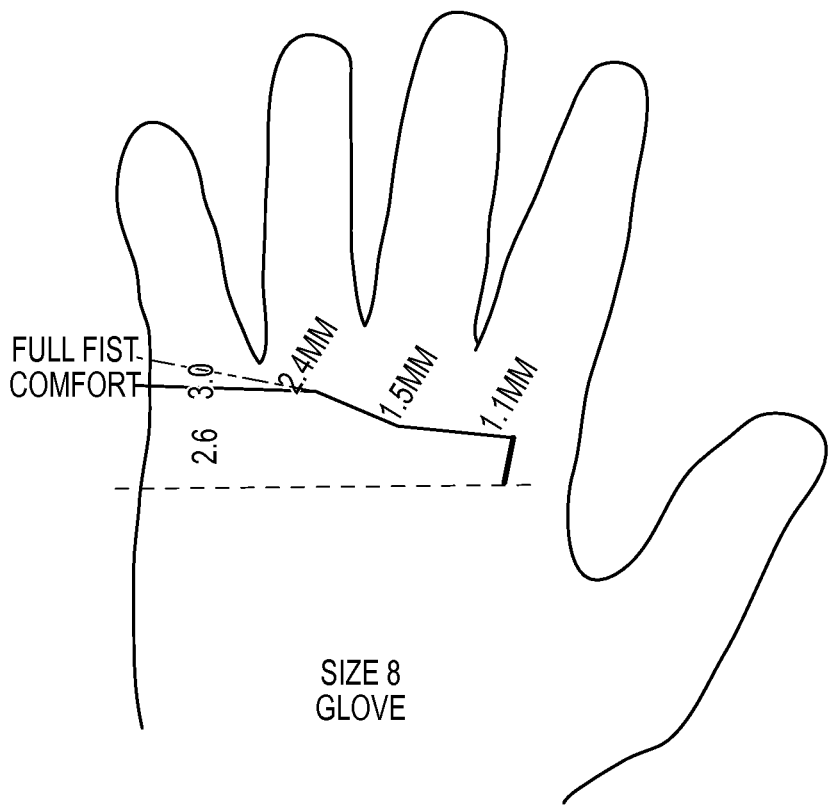
FIG. 24 illustrates an amount of stretch and location of the stretch for a size 8 glove at the MCP joints of the fingers.

FIGS. 23-24 illustrate an amount of stretch and a location for desired stretch in accordance with specific exemplary embodiments of the disclosure. In the illustrated examples, stretch for a size 6.5 glove corresponding to the MCP joints in a hand is illustrated on FIG. 23. Similarly in FIG. 24, an amount of stretch in mm is illustrated for a size 8 glove.

Materials

A glove according to various aspects of exemplary embodiments of the invention can additionally or alternatively include one or both of the following:

The material forming the glove may have varying thicknesses such that thinner portions are used at positions corresponding to one or more joints on a hand (e.g., where joints or the hand are flexed). For example, a thickness can be reduced by 5%, 10%, 25%, 35%, or 50% in any portion of the glove that must flex when the hand and/or one of the digits is opened or closed. For example, the thickness of the material in one or more joint areas or a dorsum region, or at the folds in the palm, or between fingers, or between the thumb and the index finger may be reduced as compared to a thickness of the glove material at other locations.

A glove may be comprised of multiple materials wherein a more flexible material (also called a first material) is used at positions corresponding to joints on a hand (e.g., where the digit joints or the hand are flexed). A more puncture-resistant material (also called a second material) may be used at other locations. For example, an elongation at break of the more puncture-resistant material can be about 5%, 10%, 25%, 35%, 50%, 100%, 200% or 300% less than the elongation at break of the more flexible material. The more puncture resistant second material can be 5%, 10%, 25%, 35%, 50%, 100%, 200%, or 300% more puncture resistant, e.g., as determined according to ASTM F1342. The second material may be positioned at one or more finger tips, tip of the thumb, or at any suitable location that permits the hand to open and close without much resistance.

A glove according to aspects of the invention, in addition to including any or all of the other features referenced in this application, may include portions where the glove material itself is thinner so that less force is required to stretch the thinner portion. Such a glove may also have portions of material thinner than a standard glove would have in order to be more resistant to being punctured.

A glove according to aspects of the invention, in addition to including any or all of the other features referenced in this application, may also be comprised of multiple materials, wherein one material is more flexible and is positioned at locations wherein easier flexing of the gloves is desired.

An aspect of the invention also includes the concept of placing one glove (an outer glove) over another (an inner glove) to create a double glove. A double glove could be packaged as one item in a single package thereby eliminating the packaging of the second glove.

The outer glove may be slightly larger than the inner glove in order to facilitate easier placement of one over the other. For instance a size 8 double might include a size 8 inner glove and a size 8.1 outer glove. Additionally, the inner glove may have a micro-texturing on the outside surface and/or the outer glove may have a micro-texturing on the inner surface to facilitate easier placement of one over the other.

Some specific, non-limiting examples of a surgical glove according to aspects of the invention are as follows:

1. A glove wherein at least one MCP joint is formed at a flex angle of 10-55°.
2. The glove of example 1 wherein at least two MCP joint portions are formed at a flex angle of 10-45°.
3. The glove of example 1 or 2 wherein at least one MCP joint portion is formed at a flex angle of 15-50°.
4. The glove of any of examples 1-3 wherein at least one MCP joint portion is formed at a flex angle of 20-55°.
5. The glove of any of examples 1-4 wherein at least one PIP joint portion is formed at a flex angle of 5-25°.
6. The glove of any of examples 1-5 wherein at least two PIP joint portions are formed at a flex angle of 5-25°.
7. The glove of any of examples 1-6 wherein at least one PIP joint portion is formed at a flex angle of 10-35°.
8. The glove of any of examples 1-7 wherein at least one PIP joint portion is formed at a flex angle of 15-40°.
9. The glove of any of examples 1-8 wherein at least one DIP joint portion is formed at a flex angle of 5-25°.
10. The glove of any of examples 1-9 wherein at least two DIP joint portions are formed at a flex angle of 5-25°.
11. The glove of any of examples 1-10 wherein at least one DIP joint portion is formed at a flex angle of 10-30°.
12. The glove of any of examples 1-11 wherein at least one DIP joint portion is formed at a flex angle of 15-40°.
13. The glove of any of examples 1-12 wherein the thumb MCP joint portion is formed at a flex angle of 10-45°.
14. The glove of any of examples 1-13 wherein the thumb PIP joint portion is formed at a flex angle of 20-50°.
15. A glove wherein at least one PIP joint is formed at a flex angle of 5-40°.
16. The glove of example 15 wherein at least two PIP joint portions are formed at a flex angle of 5-25°.
17. The glove of any of examples 15 or 16 wherein at least one PIP joint portion is formed at a flex angle of 10-35°.
18. The glove of any of examples 15-17 wherein at least one PIP joint portion is formed at a flex angle of 15-40°.
19. The glove of any of examples 15-18 wherein at least one DIP joint portion is formed at a flex angle of 5-25°.
20. The glove of any of examples 15-19 wherein at least two DIP joint portions are formed at a flex angle of 5-25°.
21. The glove of any of examples 15-20 wherein at least one DIP joint portion is formed at a flex angle of 10-30°.
22. The glove of any of examples 15-21 wherein at least one DIP joint portion is formed at a flex angle of 15-40°.
23. The glove of any of examples 15-22 wherein the thumb MCP joint portion is formed at a flex angle of 10-45°.
24. The glove of any of examples 15-23 wherein the thumb PIP joint portion is formed at a flex angle of 20-50°.
25. A glove wherein at least one DIP joint is formed at a flex angle of 5-25°.
26. The glove of example 25 wherein at least two DIP joint portions are formed at a flex angle of 5-25°.
27. The glove of any of examples 25-26 wherein at least one DIP joint portion is formed at a flex angle of 10-30°.
28. The glove of any of examples 25-27 wherein at least one DIP joint portion is formed at a flex angle of 15-40°.
29. The glove of any of examples 25-28 wherein the thumb MCP joint portion is formed at a flex angle of 10-45°.
30. The glove of any of examples 25-29 wherein the thumb PIP joint portion is formed at a flex angle of 20-50°.
31. A glove wherein the MCP joint of the thumb is formed at a flex angle of 10-45°.
32. The glove of example 31 wherein the PIP joint of the thumb is formed at a flex angle of 20°-50°.
33. The glove of any of examples 1-32 wherein there is a pattern between the MCP joint and PIP joint on at least one finger.
34. The glove of example 33 wherein the pattern is on the top of the at least one finger.
35. The glove of any of examples 1-33 wherein the pattern can expand to provide between $\frac{1}{16}$" and $\frac{1}{4}$" of extra material to allow for expansion of the finger.
36. The glove of any of examples 33-35 wherein the pattern is a longitudinally-extending rib.
37. The glove of any of examples 33-36 wherein there is a pattern between the MCP joint and PIP joint on a plurality of fingers.
38. The glove of example 37 wherein there is a longitudinally-extending rib between the MCP joint and PIP joint on all four fingers.
39. The glove of any of examples 1-38 wherein there is a pattern between the PIP joint and DIP joint on at least one finger.
40. The glove of claim 39 wherein the pattern is on the top of the at least one finger.
41. The glove of any of examples 39-40 wherein the pattern is a longitudinally-extending rib between the PIP joint and DIP joint.
42. The glove of example 41 wherein the rib is on the top of the at least one finger.
43. The glove of any of examples 39-42 wherein the rib can expand to provide between $\frac{1}{16}$" and $\frac{1}{4}$" of extra material to allow for expansion of the finger.
44. The glove of any of examples 39-43 wherein there is a pattern between the PIP joint and
DIP joint on a plurality of fingers.
45. The glove of example 44 wherein there is a pattern between the PIP joint and DIP joint on all four fingers.
46. The glove of examples 44-45 wherein the pattern is a longitudinally-extending rib.
47. The glove of any of examples 1-46 wherein there is a pattern between the MCP joint on the thumb and the DIP joint of the thumb.
48. The glove of example 47 wherein the pattern is on the top of the thumb.
49. The glove of any of examples 47-48 wherein the pattern can expand to provide between $\frac{1}{16}$" and $\frac{1}{4}$" of extra material to allow for expansion of the thumb.
50. The glove of any of examples 43-49 wherein the pattern is a rib extending along the longitudinal axis between the DIP joint and the IP joint of the thumb.
51. The glove of any of examples 1-50 wherein there is a plurality of patterns, with each pattern located at a different location on the glove.
52. The glove of any of examples 1-51 wherein there is a pattern between the CMC joint and the MCP joint of the thumb.
53. The glove of example 52 wherein the pattern is on the top of the thumb.
54. The glove of any of any of examples 52-53 wherein the pattern can expand to provide between $\frac{1}{16}$" and $\frac{1}{2}$" of extra material to allow for flexing of the thumb.
55. The glove of any of examples 52-54 wherein the pattern is a rib along the longitudinal axis between the CMC joint and the MCP joint of the thumb.
56. The glove of any of examples 52-55 wherein there is a plurality of patterns.

57. The glove of any of examples 1-56 that includes an outer surface and an inner surface, and a pattern on at least part of one or more of the outer surface and the inner surface, the pattern for reducing biasing forces when the hand or fingers are moved towards the closed position.
58. The glove of example 57 wherein the pattern also reduces biasing forces when the hand or fingers are moved towards the open position.
59. The glove of any of examples 57 or 58 wherein the pattern is entirely on at least part of the outer surface.
60. The glove of any of examples 57 or 58 wherein the pattern is entirely on at least part of the inner surface.
61. The glove of any of examples 33-60 wherein the pattern is selected from one or more of the group consisting of: (a) ribs, (b) raised portions, wherein the center of each raised portion is no greater than either ¼", ⅛", or 1/16" apart, (c) dimples, or (d) one or more designs.
62. The glove of any of examples 33-61 wherein the pattern is selected from one or more ribs that can provide between 1/16" and ¼" of extra material to allow for expansion while reducing biasing forces, wherein the one or more ribs can be oriented in any direction.
63. The glove of any of examples 33-61 wherein the pattern is selected from alternating raised portions that can collectively provide for 1/16" to ½" of extra material to allow for expansion while reducing biasing forces.
64. The glove of example 63 wherein the raised portions are 10 mm or less in height.
65. The glove of example 63 wherein the raised portions are 5 mm or less in height.
66. The glove of any of examples 63-65 wherein the raised portions have one or more of the following cross-sectional shapes: pyramidal, square, rectangular, semi-oval and semi-circular, and irregular.
67. The glove of any of examples 63-66 wherein each raised portion has a center and the distance between the center of each raised portion is between 1 mm and 10 mm.
68. The glove of any of examples 63-66 wherein each raised portion has a center and the distance between the center of each raised portion is between 2 mm and 5 mm.
69. The glove of example 62 wherein each rib extends 5 mm or less from the outer surface of the glove.
70. The glove of example 62 wherein each rib extends 10 mm or less from the outer surface of the glove.
71. The glove of example 61 wherein the one or more designs are selected from the group consisting of: (a) flowers, (b) letters, (c) concentric circles, (d) numbers, and (e) random designs.
72. The glove of any of examples 1-32 that includes patterns, wherein the patterns provide additional material to permit flexion of the hand while reducing biasing forces, the patterns being at one or more of the following positions on the glove: (a) portions corresponding to one or more of the MCP joints, (b) portions corresponding to one or more of the PIP joints, (c) portions corresponding to one or more of the DIP joints, (d) a portion corresponding to the space between the thumb and index finger, (e) portions corresponding to one or more spaces between any of the fingers, (f) a portion corresponding to at least part of the palm of the hand, and (g) a portion corresponding to at least part of the dorsum of the hand.
73. The glove of any of examples 1-72 wherein the pattern is formed on the dorsum side and/or the palm side of one or more of the following: the MCP joint of the index finger, the MCP joint of the middle finger, the MCP joint of the ring finger, and the MCP joint of the little finger.
74. The glove of any of examples 33-73 wherein the pattern is formed on the dorsum side and/or the palm side of one or more of the following: the PIP joint of the index finger, the PIP joint of the middle finger, the PIP joint of the ring finger, and the PIP joint of the little finger.
75. The glove of any of examples 33-74 wherein the pattern is formed on the dorsum side and/or the palm side of one or more of the following: the DIP joint of the index finger, the DIP joint of the middle finger, the DIP joint of the ring finger, and the DIP joint of the little finger.
76. The glove of any of examples 33-75 wherein the pattern is formed on the dorsum side and/or the palm side of the CMC joint of the thumb.
77. The glove of any of examples 33-76 wherein the pattern is formed on the dorsum side and/or the palm side of the MCP joint of the thumb.
78. The glove of any of examples 33-77 wherein the pattern is formed on the dorsum side and/or the palm side of the PIP joint of the thumb.
79. The glove of any of examples 33-78 wherein the pattern is formed between the thumb and index finger.
80. The glove of any of examples 33-79 wherein the pattern is formed between the index finger and middle finger.
81. The glove of any of examples 33-80 wherein the pattern is formed between the middle finger and ring finger.
82. The glove of any of examples 33-81 wherein the pattern is formed between the ring finger and little finger.
83. The glove of any of examples 33-82 wherein the pattern is formed on at least part of the palm of the hand.
84. The glove of any of examples 33-83 wherein the pattern is formed on at least part of the dorsum of the hand.
85. The glove of any of examples 33-84 wherein the pattern is formed on the palm and extends from approximately the center of the palm to the area between the thumb and index finger.
86. The glove of any of examples 33-85 wherein the pattern is formed on the entire palm of the hand.
87. The glove of any of examples 33-86 wherein the pattern is formed on the dorsum behind the little finger and ring finger.
88. The glove of any of examples 33-87 wherein the pattern is formed on the dorsum behind the little finger, the ring finger and the middle finger.
89. The glove of any of examples 33-88 wherein the pattern is formed on the dorsum behind all of the fingers, and extends at least ¼" from the MCP joints.
90. The glove of any of examples 33-89 wherein the pattern is formed on the dorsum behind all of the fingers and the thumb, and extends at least ¼" from the MCP joints on the fingers.
91. The glove of any of examples 87-90 wherein the pattern expands in width the closer it is to the little finger, and has a minimum width of at least ¼" from the MCP joint on the index finger.
92. The glove of any of examples 1-91 that is formed at a flex angle in the palm region.
93. The glove of any of examples 1-92 wherein the glove is formed at a 5-25° flex angle in the palm region.
94. The glove of any of examples 1-92 wherein the glove is formed at a 10-40° flex angle at the palm.
95. The glove of any of examples 33-91 wherein the pattern covers the index finger on the dorsum and/or palm side from the distal hand to the proximal phalanx.
96. The glove of any of examples 33-95 wherein the pattern covers the dorsum and/or the palm side of the little finger.
97. The glove of any of examples 33-96 wherein the pattern covers the dorsum side of each finger.

98. The glove of any of examples 33-97 wherein the pattern covers the palm side of each finger.
99. The glove of any of examples 33-98 wherein the pattern covers the dorsum side and/or the palm side of the thumb.
100. The glove of any of examples 72-99 wherein the pattern comprises one or more of the group selected from: (a) ribs, (b) raised portions, wherein the center of each raised portion is no greater than either ¼", ⅛", or 1/16" apart, (c) dimples, or (d) one or more designs.
101. The glove of example 100 wherein the raised portions comprise one or more of the group selected from: the one or more designs are selected from the group consisting of: (a) flowers, (b) letters, (c) concentric circles, (d) numbers, and (e) random designs.
102. The glove of any of examples 33-101 wherein each pattern present on a finger provides between 1/16" and ⅜" of additional material to reduce biasing force during flexion.
103. The glove of any of examples 33-102 wherein each pattern present on the dorsum provides between ⅛" and ½" of additional material to reduce biasing force during flexion.
104. The glove of any of examples 33-103 wherein each pattern present on the palm provides between ⅛" and ½" of additional material to reduce biasing force during flexion.
105. The glove of any of examples 33-104 wherein a pattern present between the thumb and index finger provides between ¼" and ½" of additional material to reduce biasing force during flexion.
106. The glove of any of examples 33-105 wherein a pattern present between any two fingers provides between 1/16" and ½" of additional material to reduce biasing force during flexion.
107. A glove with portions formed as follows: (a) a MCP joint of the index finger has a flex angle of 10°-30°, and (b) a PIP joint portion on the same finger is formed at a flex angle greater than the flex angle at which the MCP joint portion is formed.
108. The glove of example 107 wherein the PIP joint portion is formed at a flex angle of between 30° and 45°.
109. The glove of example 107 or 108 that includes a DIP joint portion on the same finger formed at a flex angle of less than the flex angle of the MCP joint.
110. The glove of example 110 wherein the DIP joint portion is formed at a flex angle of 0°-20°.
111. The glove of any of examples 107-110 wherein the flex angle of the MCP joint portion is 25°.
112. The glove of any of examples 107-111 wherein the flex angle of the PIP joint portion is 40°.
113. A glove with portions formed as follows: (a) a MCP joint portion of the middle finger has a flex angle of 10°-30°, and (b) a PIP joint portion on the same finger formed at a flex angle greater than the flex angle at which the MCP joint portion is formed.
114. The glove of example 113 wherein the PIP joint portion is formed at a flex angle of between 30° and 45°.
115. The glove of any of examples 113 or 114 wherein the finger includes a DIP joint formed at a flex angle of less than the flex angle of the MCP joint portion.
116. The glove of example 115 wherein the DIP joint portion is formed at a flex angle of 0°-20°.
117. The glove of any of examples 113-116 wherein the flex angle of the MCP joint portion is 25°.
118. The glove of any of examples 113-117 wherein the flex angle of the PIP joint portion is 40°.
119. A glove with portions formed as follows: (a) a MCP joint of the ring finger has a flex angle of 10°-30°, and (b) a PIP joint portion is formed at a flex angle greater than the flex angle at which the MCP joint portion is formed.
120. A glove with portions formed as follows: (a) a MCP joint of the little finger has a flex angle of 10°-30°, and (b) a PIP joint is formed at a flex angle greater than the flex angle at which the MCP joint portion is formed.
121. The glove of example 119 or 120 wherein the PIP joint portion is formed at a flex angle of between 30° and 45°.
122. The glove of example 119 or 120 wherein the DIP joint portion is formed at a flex angle of less than the flex angle of the MCP joint portion.
123. The glove of any of examples 119 or 120 that includes a DIP joint portion formed at a flex angle of 0°-20°.
124. The glove of any of examples 119-123 wherein the flex angle of the MCP joint portion is 25°.
125. The glove of any of examples 119-124 wherein the flex angle of the PIP joint portion is 40°.
126. The glove of any of examples 119-124 that further includes patterns to assist to alleviating the biasing forces associated with one or more of: (a) closing the hand, (b) opening the hand, (c) flexing or bending the fingers, or (d) moving the thumb.
127. A glove having an index finger portion, a middle finger portion, a ring finger portion, a little finger portion and a thumb portion wherein:
    (a) the section of the index finger portion corresponding to the index finger PIP joint is at an angle; and
    (b) the section of the middle finger portion corresponding to the middle finger PIP joint is formed at an angle equal to or greater than the angle of the section of the index finger portion corresponding to the index finger PIP joint.
128. A glove having an index finger portion, a middle finger portion, a ring finger portion, a little finger portion, a thumb portion, a palm portion and a dorsum portion, wherein one or more of part or all of either the index finger portion, ring finger portion, thumb portion, palm portion or dorsum portion is formed of a first material having a lower durometer and being more flexible than a second material that forms the rest of the glove.
129. The glove of example 128 that further includes one of the structures as set forth in examples 1-127 or 130-144.
130. A glove having an index finger portion, a middle finger portion, a ring finger portion, a little finger portion, a thumb portion, a palm portion and a dorsum portion, wherein one or more of part or all of either the index finger portion, ring finger portion, thumb portion, palm portion or dorsum portion is formed of a first material having a lower durometer and being more flexible than a second material that forms the rest of the glove.
131. The glove of example 130 that further includes one of the structures as set forth in examples 1-127 or 133-144.
132. The glove of either of examples 130 or 131 wherein the thinner portion(s) are between 10° and 50° thinner than the thicker portions.
133. A glove wherein one or more of the following portions is formed as follows: (a) the portion corresponding to the DIP joint of the index finger is formed at a 5-25° flex angle, (b) the portion corresponding to the DIP joint of the middle finger is at a 5-25° flex angle, (c) the portion corresponding to the DIP joint of the ring finger is formed at a 10-30° flex angle, and (d) the portion corresponding to the DIP joint of the little finger is formed at a 15-40° flex angle.

134. The glove of example 133 wherein one or more of the following portions is formed as follows: (a) the portion corresponding to the MCP joint of the thumb is formed at a flex angle of 10-45°, and (b) the portion corresponding to the PIP joint of the thumb is formed at a flex angle of 20-50°.

135. The glove of any of examples 133-134 wherein one or more of the following portions is formed as follows: (a) the portion corresponding to the MCP joint of the thumb is formed at a flex angle of 10-45°, and (b) the portion corresponding to the PIP joint of the thumb is formed at a flex angle of 20-50°.

136. The glove of any of examples 133-135 wherein the portion corresponding to the CMC joint of the thumb is formed at a flex angle of 5-25°.

137. The glove of any of examples 133-136 wherein the thumb CMC joint is positioned such that the entire thumb axis is positioned in its relaxed plane.

138. The glove of example 137 wherein the thumb is abducted out of the plane of the palm in a partially opposed position to the plane of the palm.

139. The glove of any of examples 133-138 wherein the flex angle of the DIP joint is less than the flex angle of the corresponding MCP joint.

140. The glove of example 36 wherein the rib is on the top surface of the finger.

141. The glove of example 38 wherein each rib is on the top surface of the finger.

142. The glove of example 46 wherein each rib can provide between 1/16" and 1/4" of extra material.

143. A glove formed at the natural cascading position shown in FIG. 21 plus or minus 10° for each flex angle.

144. The glove of any of examples 133-143 that further includes one or more patterns.

145. A glove wherein the flex angle of the portions of the glove corresponding to the MCP joint of each of the index finger, middle finger, ring finger and little finger is 40°-50°.

146. A glove wherein the flex angle of portions of the glove corresponding to the MCP joint of at least one of the index finger, middle finger, ring finger and/or little finger is 40°-50°.

147. The glove of any of examples 145-146 wherein the flex angle of the portions of the glove corresponding to the PIP joint of each of the index finger, middle finger, ring finger and little finger is 10°-20°.

148. The glove of any of examples 145-146 wherein the flex angle of one or more portions of the glove corresponding to the PIP joint of each index finger, middle finger, ring finger and/or little finger is 10°-20°.

149. The glove of any of examples 145-148 wherein the flex angle of the portions of the glove corresponding to the DIP joint of each of the index finger, middle finger, ring finger and little finger is 5°-25° or 10°-20°.

150. The glove of any of examples 145-148 wherein the flex angle of one or more portions of the glove corresponding to the DIP joint of one or more of the index finger, middle finger, ring finger and/or little finger is 5°-25° or 10°-20°.

151. The glove of any of examples 1-150 that is formed to provide an additional 8 mm-15 mm of material along the length of the top surface of the index finger as compared to the length of the top surface of the index finger when in its extended position and straight.

152. The glove of any of examples 1-151 that is formed to provide an additional 10 mm-18 mm of material along the length of the top surface of the middle finger as compared to the length of the top surface of the middle finger when in its extended position and straight.

153. The glove of any of examples 1-152 that is formed to provide an additional 15 mm-30 mm of material along the length of the top surface of the ring finger as compared to the length of the top surface of the ring finger when in its extended position and straight.

154. The glove of any of examples 1-153 that is formed to provide an additional 20 mm-40 mm of material along the length of the top surface of the little finger as compared to the length of the top surface of the little finger when in its extended position and straight.

155. The glove of any of examples 151-154 wherein 40°-60° of the additional material is provided by flex angles at one or more joints of the finger.

156. The glove of example 155 wherein the remaining extra material is provided by patterns at one or more joints of the finger.

157. The glove of any of examples 151-154 wherein all of the additional material is provided by the flex angles at one or more joints of the finger.

158. The glove of any of examples 151-154 wherein all of the additional material is provided by patterns at one or more joints of the finger.

159. The glove of any of examples 156-158 wherein the extra material provided by patterns is provided such that 40-60% of the extra material is at the MCP joint.

160. The glove of any of examples 151-159 wherein 20-30% of the extra material is at the DIP joint.

161. The glove of any of examples 156-160 wherein all of the patterns are ribs.

162. The glove of any of examples 1-161 wherein there are four separate, non-connected ribs at the thumb PIP joint.

163. The glove of any of examples 1-162 wherein there are at least four separate, non-connected ribs at the index finger MCP joint.

164. The glove of any of examples 1-163 wherein there are at least six separate, non-connected ribs at the MCP joint of the middle finger and index finger.

165. The glove of any of examples 1-164 wherein there are at least seven separate, non-connected ribs at the MCP joint of the little finger.

166. The glove of any of examples 1-165 wherein there are at least three separate, non-connected ribs in the palm portion.

167. The glove of example 166 wherein the uppermost rib in the palm portion extends from at least under the index finger to under the little finger.

168. The glove of any of examples 166-167 wherein the center rib of the palm portion extends from at least the index finger to a location between the little finger and ring finger.

169. The glove of any of examples 166-168 wherein the lower rib of the palm portion extends at least from the index finger to under the ring finger.

170. The glove of any of examples 166-169 wherein at least one rib of the palm portion extends into the space between the thumb and index finger.

171. The glove of any of examples 1-170 that further includes a rib extending along the muscle of the thumb.

172. The glove of any of examples 1-171 wherein there are three separate, non-connected ribs at one or more of the thumb IP joint, the index finger DIP joint, the middle finger DIP joint, the ring finger DIP joint, the little finger DIP joint, the index finger PIP joint, the middle finger PIP joint, the ring finger PIP joint, and the little finger PIP joint.

173. The glove of example 172 wherein the ribs extend completely around the joint.
174. The glove of any of examples 162-165 wherein each rib is curved and the center of each rib is 1 mm-3 mm farther from the distal end of the finger than at least one end of the rib.
175. The glove of any of examples 162-165 and 174 wherein the ribs are only positioned on the top of the MCP joint.
176. The glove of any of examples 1-175 wherein the portion located at the MCP joint of the index finger provides 2 mm-15 mm or 2 mm-11 mm of extra material.
177. The glove of any of examples 1-176 wherein the portion located at the MCP joint of the middle finger provides 3 mm-20 mm or 3 mm-15 mm of extra material.
178. The glove of any of examples 1-177 wherein the portion located at the MCP joint of the ring finger provides 4 mm-25 mm or 4 mm-24 mm of extra material.
179. The glove of any of examples 1-178 wherein the portion located at the MCP joint of the little finger provides 5 mm-30 mm or 5 mm-35 mm of extra material.
180. The glove of any of examples 1-179 wherein the portion located at the PIP joint of the index finger provides 1 mm-8 mm or 1 mm-10 mm of extra material.
181. The glove of any of examples 1-180 wherein the portion located at the DIP joint of the index finger provides 1 mm-8 mm or 1 mm-10 mm of extra material.
182. The glove of any of examples 1-181 wherein the portion located at the PIP joint of the middle finger provides 1 mm-8 mm or 1 mm-10 mm of extra material.
183. The glove of any of examples 1-182 wherein the portion located at the DIP joint of the middle finger provides 1 mm-8 mm or 1 mm-10 mm of extra material.
184. The glove of any of examples 1-183 wherein the portion located at the PIP joint of the ring finger provides 1 mm-8 mm or 1 mm-10 mm of extra material.
185. The glove of any of examples 1-184 wherein the portion located at the PIP joint of the ring finger provides 1 mm-8 mm or 1 mm-10 mm of extra material.
186. The glove of any of examples 1-185 wherein the portion located at the PIP joint of the little finger provides 1 mm-8 mm or 1 mm-10 mm of extra material.
187. The glove of any of examples 1-186 wherein the portion located at the thumb PIP joint provides 5 mm-20 mm of extra material.
188. The glove of any of examples 1-187 wherein the portion located at the thumb IP joint provides 8 mm-20 mm of extra material.
189. The glove of any of examples 1-188 wherein a pattern between any of the fingers provides 20 mm-200 mm of extra material.
190. The glove of any of examples 1-189 wherein a pattern between the index finger and thumb provides 30 mm-350 mm of extra material.
191. The glove of any of examples 175-190 wherein the extra material is provided by a pattern.
192. The glove of any of examples 175-190 wherein the extra material is provided by the shape of the glove.
193. The glove of any of examples 175-190 wherein the extra material is provided by a combination of a pattern and the shape of the glove.
194. The glove according to any of examples 1-193 wherein the thickness of the material forming the glove is reduced by 5%-50% at one or more of the following positions: (a) at least one MCP joint of the fingers, (b) at least one PIP joint of the fingers, and (c) at least one DIP joint of the fingers.
195. The glove according to any of examples 1-194 wherein the thickness of the material forming the glove is reduced by 5%-50% at one or more of the following positions: (1) the PIP joint of the thumb, and (b) the IP joint of the thumb.
196. The glove according to any of examples 1-195 wherein the thickness of the material forming the glove is reduced by 5%-50% at one or more of the following positions: (a) the palm, and (b) at least one of the spaces between any two fingers and/or the index finger and thumb.
197. The glove according to any of examples 1-196 that includes a first material and a second material, wherein the second material is 50%-300% or more puncture resistant than the first material as measured according to ASTM F1342, and the second material is positioned at one or more of the finger tips and tip of the thumb.
198. The glove according to example 197 wherein the second material is positioned on the palm side of one or more fingers between the finger joints.
199. The glove according to either of examples 197-198 wherein the second material is positioned on the palm side of the thumb between the joints.
200. The glove according to any of examples 197-199 wherein the second material is positioned on the palm and extends ¼" or more from the MCP joint of each finger towards the center of the palm.
201. The glove according to any of examples 197-200 wherein the second material is positioned on the palm region of the muscle of the thumb.
202. The glove according to example 161 wherein there are between 2-5 separate, non-connected ribs at the thumb PIP joint.
203. The glove according to any of examples 161 or 202 wherein there are between 2-6 separate, non-connected ribs at the index finger MCP joint.
204. The glove according to any of examples 161 or 202-203 wherein there are between 2-6 separate, non-connected ribs at the middle finger MCP joint.
205. The glove according to any of examples 161 or 202-204 wherein there are between 2-7 separate, non-connected ribs at the ring finger MCP joint.
206. The glove according to any of examples 161 or 202-205 wherein there are between 2-8 separate, non-connected ribs at the little finger MCP joint.
207. The glove of any of examples 1-165 or 202-206 wherein there are between 1 and 5 separate, non-connected ribs in the palm portion of the glove.
208. The glove of any of examples 1-171 wherein there are 2-5 separate, non-connected ribs at one or more of the thumb IP joint, the index finger DIP joint, the middle finger DIP joint, the ring finger DIP joint, the little finger DIP joint, the index finger PIP joint, the middle finger PIP joint, the ring finger PIP joint, and the little finger PIP joint.

Having thus described preferred embodiments of the invention, other variations and embodiments that do not depart from the spirit of the invention will become apparent to those skilled in the art. The scope of the present invention is thus not limited to any particular embodiment, but is instead set forth in the appended claims and the legal equivalents thereof. Unless expressly stated in the written description or claims, the steps of any method recited in the claims may be performed in any order capable of yielding the desired result.

What is claimed is:

1. A medical glove, comprising:
a molded elastomeric material having a thickness between from 0.14 mm to 0.3 mm and comprising one or more of latex, polychloroprene, neoprene, polyisoprene, styrene butadiene, styrene ethylene butadiene, nitrile, and vinyl polyvinylchloride, and the glove including:
a body portion, a set of finger portions, and a thumb portion; and the finger portions including an index finger portion, a middle finger portion, a ring finger portion and a little finger portion;
the body portion having a proximal opening and a distal area including respective finger openings for each of the finger portions where the finger portions are joined at the finger openings to the body portion, and the finger portions each extend along a long axis away from the finger opening, and the body portion includes a palm region, and a dorsum region which has a lateral side and a medial side and is connected on the lateral side and on the medical side to the palm region, and includes a thumb opening into the thumb portion where the thumb portion is joined at the thumb opening to the body portion and the thumb portion extends along a long axis away from the thumb opening;
the finger portions each sequentially include a MCP joint portion, a proximal phalange portion, a PIP joint portion, a middle phalange portion, a DIP joint portion, and a distal phalange portion; and the thumb portion sequentially includes a MCP joint portion, a proximal phalange portion, an IP joint portion, and a distal phalange portion;
wherein for each finger portion, the MCP joint portion, the PIP joint portion and the DIP joint portion are each formed at an angle along the long axis of the finger portion so as to collectively curve the finger portion toward the palm region, and for the thumb portion, the MCP joint portion and the IP joint portion are each formed at an angle along the long axis of the thumb portion so as to collectively curve the thumb portion toward the palm region;
wherein for each finger portion, the angle of the MCP joint portion is greater than the angle for the respective PIP joint portion and for the respective DIP joint portion for each finger portion;
wherein the angle of the index finger MCP joint portion is greater than the angle of the little finger MCP joint portion;
wherein the dorsum region includes a pattern comprising at least one projection of material proximal to the finger opening for each finger portion and there are more projections of material proximal to the opening of the little finger opening than there are proximal to the opening of the index finger opening;
wherein each of the finger portions and the thumb portion includes at least one radial expansion feature which is a projection of material which extends in the direction of the long axis so as to accommodate a radial expansion in diameter in a flexed position of the finger portion and of the thumb portion; and
wherein each of the finger portions includes at least one longitudinal expansion feature which is at least one projection of material which extends across the long axis of the finger portion at one or more of the MCP joint portion, the PIP joint portion, and the DIP joint portion so as to accommodate a longitudinal expansion in a flexed position of the finger portion and of the thumb portion includes at least one longitudinal expansion feature which is at least one projection of material which extends across the long axis of the thumb portion at one or more of the MCP joint portion and the IP joint portion so as to accommodate a longitudinal expansion in a flexed position of the thumb portion.

2. A medical glove as set forth in claim 1, wherein for each finger portion, the at least one radial expansion feature comprises the proximal phalange portion including a longitudinal rib which ends at the MCP portion and the PIP portion.

3. A medical glove as set forth in claim 1, wherein for each finger portion, the at least one radial expansion feature comprises the middle phalange portion including a longitudinal rib which ends at the PIP portion and the DIP portion.

4. A medical glove as set forth in claim 1, wherein for each finger portion, the at least one radial expansion feature comprises the distal phalange portion including a longitudinal rib which ends at the DIP portion at one end.

5. A medical glove as set forth in claim 1, wherein for the thumb portion, the at least one radial expansion feature comprises the proximal phalange portion including a longitudinal rib which ends at the MCM portion and the IP portion.

6. A medical glove as set forth in claim 1, wherein for the thumb portion, the at least one radial expansion feature comprises the distal phalange portion including a longitudinal rib which ends at the DIP portion at one end.

7. A medical glove, comprising:
a molded elastomeric material having a thickness of from 0.14 mm to 0.3 mm and comprising one or more of latex, polychloroprene, neoprene, polyisoprene, styrene butadiene, styrene ethylene butadiene, nitrile, and vinyl polyvinylchloride, and the glove including:
a body portion, a set of finger portions, and a thumb portion; and the finger portions including an index finger portion, a middle finger portion, a ring finger portion and a little finger portion;
the body portion having a proximal opening and a distal area including respective finger openings for each of the finger portions where the finger portions are joined at the finger openings to the body portion, and the finger portions each extend along a long axis away from the finger opening, and the body portion includes a palm region, and a dorsum region which has a lateral side and a medial side and is connected on the lateral side and on the medial side to the palm region, and includes a thumb opening into the thumb portion where the thumb portion is joined at the thumb opening to the body portion and the thumb portion extends along a long axis away from the thumb opening;
the finger portions each sequentially include a MCP joint portion, a proximal phalange portion, a PIP joint portion, a middle phalange portion, a DIP joint portion, and a distal phalange portion; and the thumb portion sequentially includes a MCP joint portion, a proximal phalange portion, an IP joint portion, and a distal phalange portion;
wherein for each finger portion, the MCP joint portion, the PIP joint portion and the DIP joint portion are each formed at an angle along the long axis of the finger portion so as to collectively curve the finger portion toward the palm region, and for the thumb portion, the MCP joint portion and the IP joint portion are each formed at an angle along the long axis of the thumb portion so as to collectively curve the thumb portion toward the palm region;

wherein for each finger portion, the angle of the MCP joint portion is greater than the angle for the respective PIP joint portion and for the respective DIP joint portion for each finger portion;

wherein the angle of the index finger MCP joint portion is greater than the angle of the little finger MCP joint portion;

wherein the dorsum region includes a pattern comprising at least one projection of material proximal to the finger opening for each finger portion and there are more projections of material proximal to the opening of the little finger portion than there are proximal to the opening of the index finger portion;

wherein each of the finger portions and the thumb portion includes at least one radial expansion feature which is a projection of material which extends in the direction of the long axis so as to accommodate a radial expansion in diameter in a fully flexed position of the finger portion and of the thumb portion; and wherein each of the finger portions and the thumb portion includes at least one longitudinal expansion feature which comprise a plurality of projections of material which respectively extend transverse to the long axis of the finger portion or to the long axis of the thumb portion at each of the MCP joint portion, the PIP joint portion and the DIP joint portion for each finger portion and at each of the MCP joint portion and the IP joint portion for the thumb portion, so as to accommodate a longitudinal expansion in a flexed position of the finger portion and of the thumb portion.

8. A medical glove as set forth in claim 7, wherein the index finger portion has a top surface and the longitudinal expansion feature provides for from 8 mm to 15 mm of material at the top surface of the index finger portion.

9. A medical glove as set forth in claim 8, wherein a second longitudinal expansion feature provides for 2 mm to 15 mm of material at the MCP joint of the index finger portion.

10. A medical glove as set forth in claim 9, wherein the second longitudinal expansion feature provides for 2 mm to 11 mm of material at the MCP joint of the index finger portion.

11. A medical glove as set forth in claim 8, wherein a second longitudinal expansion feature provides for 4 mm to 25 mm of material at the MCP joint of the ring finger portion.

12. A medical glove as set forth in claim 11, wherein the second longitudinal expansion feature provides for 4 mm to 24 mm of material at the MCP joint of the ring finger portion.

13. A medical glove as set forth in claim 8, wherein a second longitudinal expansion feature provides for 5 mm to 35 mm of material at the MCP joint of the little finger portion.

14. A medical glove as set forth in claim 13, wherein the second longitudinal expansion feature provides for 5 mm to 30 mm of material at the MCP joint of the little finger portion.

15. A medical glove as set forth in claim 8, wherein a second longitudinal expansion feature provides for 1 mm to 10 mm of material at the PIP joint of the index finger portion.

16. A medical glove as set forth in claim 15, wherein the second longitudinal expansion feature provides for 1 mm to 8 mm of material at the PIP joint of the index finger portion.

17. A medical glove as set forth in claim 8, wherein a second longitudinal expansion feature provides for 1 mm to 10 mm of material at the PIP joint of the middle finger portion.

18. A medical glove as set forth in claim 17, wherein the second longitudinal expansion feature provides for 1 mm to 8 mm of material at the PIP joint of the middle finger portion.

19. A medical glove as set forth in claim 8, wherein a second longitudinal expansion feature provides for 1 mm to 10 mm of material at the PIP joint of the ring finger portion.

20. A medical glove as set forth in claim 19, wherein the second longitudinal expansion feature provides for 1 mm to 8 mm of material at the PIP joint of the ring finger portion.

21. A medical glove as set forth in claim 8, wherein a second longitudinal expansion feature provides for 1 mm to 10 mm of material at the PIP joint of the little finger portion.

22. A medical glove as set forth in claim 21, wherein the second longitudinal expansion feature provides for 1 mm to 8 mm of material at the PIP joint of the little finger portion.

23. A medical glove as set forth in claim 8, wherein a second longitudinal expansion feature provides for 1 mm to 10 mm at the DIP joint of the index finger portion.

24. A medical glove as set forth in claim 23; wherein the second longitudinal expansion feature provides for 1 mm to 8 mm of material at the DIP joint of the index finger portion.

25. A medical glove as set forth in claim 8, wherein a second longitudinal expansion feature provides for 1 mm to 10 mm of material at the DIP joint of the middle finger portion.

26. A medical glove as set forth in claim 25, wherein the second longitudinal expansion feature provides for 1 mm to 8 mm of material at the DIP joint of the middle finger portion.

27. A medical glove as set forth in claim 8, wherein a second longitudinal expansion feature provides for 1 mm to 10 mm of material at the DIP joint of the ring finger portion.

28. A medical glove as set forth in claim 27, wherein the second longitudinal expansion feature provides for 1 mm to 8 mm of material at the DIP joint of the ring finger portion.

29. A medical glove as set forth in claim 8, wherein a second longitudinal expansion feature provides for 1 mm to 10 mm of material at the DIP joint of the little finger portion.

30. A medical glove as set forth in claim 29, wherein the second longitudinal expansion feature provides for 1 mm to 8 mm of material at the DIP joint of the little finger portion.

31. A medical glove as set forth in claim 8, wherein a second longitudinal expansion feature provides for 5 mm to 20 mm of material at the PIP joint of the thumb portion.

32. A medical glove as set forth in claim 31, wherein the second longitudinal expansion feature provides for 8 mm to 20 mm of material at the IP joint of the thumb portion.

33. A medical glove as set forth in claim 7, wherein the ring finger portion has a top surface and the longitudinal expansion feature provides for from 15 mm to 30 mm of material at the top surface of the ring finger portion.

34. A medical clove as set forth in claim 33, wherein a second longitudinal expansion feature provides for 3 mm to 20 mm of material at the MCP joint of the middle finger portion.

35. A medical glove as set forth in claim 34, wherein the second longitudinal expansion feature provides for 3 mm to 15 mm of material at the MCP joint of the middle finger portion.

36. A medical glove as set forth in 7, wherein the little finger has a top surface and the longitudinal expansion feature provides for from 20 mm to 40 mm of material at the top surface of the little finger portion.

37. A glove, comprising:
a molded elastomeric material having a thickness between of from 0.14 mm to 0.3 mm and comprising one or more of latex, polychloroprene, neoprene, polyisoprene, styrene butadiene, styrene ethylene butadiene, nitrile, and vinyl polyvinylchloride, and the glove including:
a body portion, a set of finger portions; and a thumb portion; and the finger portions including an index finger portion, a middle finger portion, a ring finger portion and a little finger portion;
the body portion having a proximal opening and a distal area including respective finger openings for each of the finger portions where the finger portions are joined at the finger openings to the body portion, and the finger portions each extend along a long axis away from the finger opening, and the body portion includes a palm region, and a dorsum region which has a lateral side and a medal side and is connected on the lateral side and on the medial side to the palm region; and includes a thumb opening into the thumb portion where the thumb portion is joined at the thumb opening to the body portion and the thumb portion extends along a long axis away from the thumb opening;
the finger portions each sequentially include a MCP joint portion, a proximal phalange portion, a PIP joint portion, a middle phalange portion, a DIP joint portion, and a distal phalange portion; and the thumb portion sequentially includes a MCP joint portion, a proximal phalange portion, an IP joint portion, and a distal phalange portion;
wherein for each finger portion, the MCP joint portion, the PIP joint portion and the DIP joint portion are each formed at an angle along the long axis of the finger portion so as to collectively curve the finger portion toward the palm region, and for the thumb portion, the MCP joint portion and the IP joint portion are each formed at an angle along the long axis of the thumb portion so as to collectively curve the thumb portion toward the palm region;
wherein for each finger portion, the angle of the MCP joint portion is greater than the angle for the respective PIP joint portion and for the respective DIP joint portion for each finger portion;
wherein the angle of the index finger MCP joint portion is greater than the angle of the little finger MCP joint portion;
wherein the dorsum region or the palm region includes a pattern of material comprising at least one projection proximal to the finger opening for each finger portion and such that the pattern of material proximal to the opening of the little finger portion provides more material than the pattern of material proximal to the opening of the index finger portion;
wherein each of the finger portions and the thumb portion includes at least one radial expansion feature which is a projection of material which extends in the direction of the long axis so as to accommodate a radial expansion in diameter in a fully flexed position of the finger portion and of the thumb portion; and
wherein each of the finger portions includes at least one longitudinal expansion feature which is at least one projection of material which extends across the long axis of the finger portion at one or more of the MCP joint portion, the PIP joint portion, and the DIP joint portion so as to accommodate a longitudinal expansion in a flexed position of the finger portion and the thumb portion includes at least one longitudinal expansion feature which is at least one projection of material which extends across the long axis of the thumb portion at one or more of the MCP joint portion and the IP joint portion so as to accommodate a longitudinal expansion in a flexed position of the thumb portion.

* * * * *

UNITED STATES PATENT AND TRADEMARK OFFICE
CERTIFICATE OF CORRECTION

PATENT NO. : 10,130,438 B2  
APPLICATION NO. : 14/133424  
DATED : November 20, 2018  
INVENTOR(S) : Lloyd P. Champagne et al.

Page 1 of 1

It is certified that error appears in the above-identified patent and that said Letters Patent is hereby corrected as shown below:

In the Drawings

FIG. 22, "80% FEMALE" should read --80% MALE--.

In the Claims

Claim 1, Line 20, delete "medical" and replace it with --medial--, and in Line 66, delete "of" after the word and.

Signed and Sealed this  
Twenty-sixth Day of February, 2019

Andrei Iancu  
*Director of the United States Patent and Trademark Office*